(12) United States Patent
Kawada et al.

(10) Patent No.: US 11,325,895 B2
(45) Date of Patent: *May 10, 2022

(54) CRYSTALS OF TETRAHYDRONAPHTHYL UREA DERIVATIVE

(71) Applicant: MOCHIDA PHARMACEUTICAL CO., LTD., Tokyo (JP)

(72) Inventors: Yuji Kawada, Tokyo (JP); Fumihiko Saitoh, Tokyo (JP); Hiroshi Nagasue, Tokyo (JP); Tsutomu Satoh, Tokyo (JP)

(73) Assignee: MOCHIDA PHARMACEUTICAL CO., LTD., Tokyo (JP)

( * ) Notice: Subject to any disclaimer, the term of this patent is extended or adjusted under 35 U.S.C. 154(b) by 4 days.

This patent is subject to a terminal disclaimer.

(21) Appl. No.: 16/647,223

(22) PCT Filed: Sep. 13, 2018

(86) PCT No.: PCT/JP2018/034021
§ 371 (c)(1),
(2) Date: Jun. 10, 2020

(87) PCT Pub. No.: WO2019/054451
PCT Pub. Date: Mar. 21, 2019

(65) Prior Publication Data
US 2020/0308136 A1    Oct. 1, 2020

(30) Foreign Application Priority Data
Sep. 15, 2017    (JP) .............................. JP2017-178030

(51) Int. Cl.
C07D 401/04    (2006.01)
(52) U.S. Cl.
CPC ........ C07D 401/04 (2013.01); *C07B 2200/13* (2013.01)
(58) Field of Classification Search
CPC ..... C07D 401/04; C07D 213/89; A61P 37/06; A61P 43/00; C07C 213/10
See application file for complete search history.

(56) References Cited

U.S. PATENT DOCUMENTS

| | | | |
|---|---|---|---|
| 10,399,945 B2 * | 9/2019 | Saitoh ........................ | A61P 1/16 |
| 10,927,079 B2 * | 2/2021 | Kawada ..................... | A61P 1/04 |
| 2016/0229850 A1 | 8/2016 | Cooke et al. | |
| 2016/0280692 A1 | 9/2016 | Andrews et al. | |
| 2016/0297796 A1 | 10/2016 | Allen et al. | |
| 2016/0355521 A1 | 12/2016 | Allen et al. | |
| 2017/0087156 A1 | 3/2017 | Allen et al. | |
| 2019/0023657 A1 | 1/2019 | Saitoh et al. | |
| 2019/0270749 A1 | 9/2019 | Allen et al. | |
| 2019/0337897 A1 | 11/2019 | Saitoh et al. | |

FOREIGN PATENT DOCUMENTS

| | | | |
|---|---|---|---|
| WO | WO 2014/078325 A1 | 5/2014 | |
| WO | WO 2014/078378 A1 | 5/2014 | |
| WO | WO 2014/078454 A1 | 5/2014 | |
| WO | WO 2015/039333 A1 | 3/2015 | |
| WO | WO 2015/175788 A1 | 11/2015 | |
| WO | WO 2018/199166 A1 | 11/2018 | |

OTHER PUBLICATIONS

Aalto et al., "Nerve Growth Factor in Serum of Children With Systemic Lupus Erythematosus is Correlated With Disease Activity", Cytokine, vol. 20, No. 3 Nov. 7, 2002, pp. 136-139.
Althaus, "Remyelination in multiple sclerosis: a new role for neurotrophins?", Progress in Brain Research, vol. 146, ISSN 0079-6123, 2004, pp. 415-432.
Ashraf et al., "Selective inhibition of tropomyosin-receptor-kinase A (TrkA) reduces pain and joint damage in two rat models of inflammatory arthritis", Arthritis Research & Therapy (2016) 18:97, pages 1-11.
Brodeur, "Neuroblastoma: Biological Insights Into a Clinical Enigma", Nature Reviews Cancer, vol. 3, Mar. 2003, pp. 203-216.
Carr et al., "Neurotrophins and asthma", Current Opinion in Pulmonary Medicine, vol. 7, 2001, pp. 1-7.
Chang et al., "Anti-nerve growth factor in pain management: current evidence", Journal of Pain Research, 2016:9 pp. 373-383.
Crowley et al., "Mice Lacking Nerve Growth Factor Display Perinatal Loss of Sensory and Sympathetic Neurons yet Develop Basal Forebrain Cholinergic Neurons", Cell, vol. 76, Mar. 25, 1994, pp. 1001-1011.
D'Arco et al., "Neutralization of Nerve Growth Factor Induces Plasticity of ATP-Sensitive $P2X_3$ Receptors of Nociceptive Trigeminal Ganglion Neurons", The Journal of Neuroscience, Aug. 1, 2007, 27(31), pp. 8190-8201.
Demir et al., "Nerve growth factor & TrkA as novel therapeutic targets in cancer", Biochimica et Biophysica Acta, vol. 1866 (2016), pp. 37-50.
Gruber-Olipitz et al., "Synthesis, Chaperoning, and Metabolism of Proteins Are Regulated by NT-3/TrkC Signaling in the Medulloblastoma Cell Line DAOY", Journal of Proteome Research 2008, vol. 7, pp. 1932-1944.
International Search Report for PCT/JP2018/034021 (PCT/ISA/210) dated Nov. 27, 2018.
Kamiya et al., "Prognostic value of tropomyosin-related kinases A, B, and C in gastric cancer", Clinical & Translational Oncology, 2016, vol. 18, pp. 599-607.
Klein, "Role of neurotrophins in mouse neuronal development", The FASEB Journal, vol. 8, Jul. 1994, pp. 738-744.

(Continued)

*Primary Examiner* — Brian E McDowell
(74) *Attorney, Agent, or Firm* — Birch, Stewart, Kolasch & Birch, LLP

(57) ABSTRACT

Provided are type I, III, V and VI crystals of 1-((1R,2R)-2-hydroxy-4,4-dimethyl-1,2,3,4-tetrahydronaphthalen-1-yl)-3-(5-methyl-6-(2-methylpyrimidin-5-yl)-2-phenylpyridin-3-yl)urea which are useful as bulk pharmaceutical crystals. Also provided are type I, III, V and VI crystals of 1-((1R,2R)-2-hydroxy-4,4-dimethyl-1,2,3,4-tetrahydronaphthalen-1-yl)-3-(5-methyl-6-(2-methylpyrimidin-5-yl)-2-phenylpyridin-3-yl)urea having excellent TrkA inhibitory effect, medicines and medicinal composition containing these crystals, and a method for producing these crystals.

10 Claims, 6 Drawing Sheets

(56) References Cited

OTHER PUBLICATIONS

McKelvey et al., "Nerve growth factor-mediated regulation of pain signalling and proposed new intervention strategies in clinical pain management", Journal of Neurochemistry, 2013, vol. 124, pp. 276-289.
Di Mola et al., "Nerve growth factor and Trk high affinity receptor (TrkA) gene expression in inflammatory bowel disease", Gut 2000, vol. 46, pp. 670-678.
Patapoutian et al., "Trk receptors: mediators of neurotrophin action", Current Opinion in Neorobiology, 2001, vol. 11, pp. 272-280.
Prakash et al., "Neurotrophins in lung health and disease", NIH Public Access, Author Manuscript, Published in final edited form as: Expert Rev Respir Med. Jun. 2010; vol. 4(3): 395-411, pp. 1-28.
Rapp et al., "Analgesia Via Blockade of NGF/TrkA Signaling Does Not Influence Fracture Healing in Mice", Journal of Orthopaedic Research, Aug. 2015, pp. 1235-1241.
Roblin et al., "Topical TrkA Kinase Inhibitor CT327 is an Effective, Novel Therapy for the Treatment of Pruritus due to Psoriasis: Results from Experimental Studies, and Efficacy and Safety of CT327 in a Phase 2b Clinical Trial in Patients with Psoriasis", Acta Derm Venereol, 2015, vol. 95, pp. 542-548.
Sabsovich et al., "Effect of anti-NGF antibodies in a rat tibia fracture model of complex regional pain syndrome type I", NIH Public Access Author Manuscript, Published in final edited form as: Pain, Aug. 15, 2008; vol. 138(1): 47-60, pp. 1-24.
Vaishnavi et al., "TRKing down an old oncogene in a new era of targeted therapy", NIH Public Access, Author Manuscript, Published in final edited form as: Cancer Discov., Jan. 2015; vol. 5(1): 25-34, pp. 1-19.
Written Opinion of the International Searching Authority for PCT/JP2018/034021 (PCT/ISA/237) dated Nov. 27, 2018.
Zhang et al., "Paradoxical Effect of TrkA Inhibition in Alzheimer's Disease Models", NIH Public Access, Author Manuscript, Published in final edited form as: J Alzheimers Dis., 2014: vol. 40(3): 605-617, pp. 1-20.

\* cited by examiner

Powder X-ray diffraction pattern of type I crystal

FT-IR spectral data of type I crystal

Powder X-ray diffraction pattern of type III crystal

FT-IR spectral data of type III crystal

Powder X-ray diffraction pattern of type V crystal

FT-IR spectral data of type V crystal

Powder X-ray diffraction pattern of type VI crystal

Spectral data of DSC and TGA of type I crystal

Micrograph of type I crystal

Spectral data of DSC and TGA of type III crystal

Spectral data of DSC and TGA of type V crystal

Micrograph of type V crystal

CRYSTALS OF TETRAHYDRONAPHTHYL UREA DERIVATIVE

TECHNICAL FIELD

The present invention relates to novel crystalline forms (type I, III, V and VI crystals) of 1-((1R,2R)-2-hydroxy-4,4-dimethyl-1,2,3,4-tetrahydronaphthalen-1-yl)-3-(5-methyl-6-(2-methylpyrimidin-5-yl)-2-phenylpyridin-3-yl) urea (hereafter also referred to as compound (1)), which is a tropomyosin receptor kinase A (TrkA) inhibitor and is a tetrahydronaphthylurea derivative being useful as a prevention and/or therapeutic agent for pain, etc., methods of producing these crystals, and pharmaceutical compositions containing the crystals.

BACKGROUND ART

Tropomyosin receptor kinase (Trk) is a neurotrophin (NT) receptor tyrosine kinase having an extracellular neurotrophin (NT) binding domain and an intracellular kinase domain, and is classified into TrkA, a receptor for nerve growth factor (NGF), TrkB, a receptor for brain-derived neurotrophic factor (BDNF) and NT-4/5, and TrkC, a receptor for NT-3. These Trk receptors are highly expressed in nervous tissue and are reported to be involved in neuronal differentiation and maintenance, and signal transduction (Non-Patent Document 1).

NGF is known to increase in concentration in painful diseases such as arthritis, pancreatitis, cystitis, chronic headache, diabetic neuropathy and cancer, and is also reported to induce pain in humans and rats to which NGF is administered (Non-Patent Document 2). In addition, it is considered that the NGF/TrkA pathway is strongly involved in the onset of pain in vivo, because it is known that NGF or TrkA loss-of-function mutation cause congenital analgesia (Non-Patent Document 3) and that NGF or TrkA knockout mice eliminate pain symptoms (Non-Patent Documents 4 and 5).

Inhibitors of the NGF/TrkA pathway, such as anti-NGF antibody, anti-TrkA antibody, and small-molecule Trk inhibitors, have been shown to improve a variety of pain symptoms in clinical and non-clinical studies. For example, it has been reported to be effective in pain associated with osteoarthritis, chronic low back pain, rheumatoid arthritis, fracture, interstitial cystitis and chronic pancreatitis, neuropathic pain, cancer pain, complex regional pain syndrome, migraine, and other pain (Non-Patent Documents 2, and 6-9).

Trk receptors containing Trk A are known to be involved in a variety of cancers including neuroblastoma, ovarian cancer, colorectal cancer, melanoma, head and neck cancer, gastric cancer, lung cancer, breast cancer, glioblastoma, astrocytoma, medulloblastoma, cholangiocarcinoma, secretory breast cancer, salivary gland cancer, prostate cancer, pancreatic cancer, thyroid papillary carcinoma, adult myeloid leukemia, etc. by mutations including overexpression, activation, and gene fusion. Trk inhibitors have been shown to inhibit tumor growth in clinical and non-clinical studies (Non-Patent Documents 10 to 14).

TrkA receptors are also expressed in inflammatory cells such as mast cells and eosinophils, monocytes, macrophages, immunocompetent cells such as T cells and B cells, and central nervous cells including cholinergic neurons. The NGF/TrkA pathway has been reported to be involved in diseases such as asthma, rhinitis, atopic dermatitis, ulcerative colitis, Crohn's disease, psoriasis, multiple sclerosis, systemic lupus erythematosus, and Alzheimer's disease (Non-Patent Documents 15 to 21).

For these reasons, the creation of drugs with TrkA inhibitory activity may be applicable to the treatment of pain, cancer, inflammatory diseases, allergic diseases, autoimmune diseases and the like, and may be a novel type of therapeutic and/or prevention agent.

Derivatives having an urea structure exerting an inhibitory effect on TrkA are disclosed in WO2015/175788 (Patent Document 1), WO2015/039333 (Patent Document 2), WO2014/078378 (Patent Document 3), and WO2014/078325 (Patent Document 4). However, any of these disclosed derivatives is not compound having a tetrahydronaphthyl structure which is a characteristic structure of the present invention, and there is no disclosure or suggestion for a compound having a tetrahydronaphthyl structure.

WO 2014/078454 (Patent Document 5) discloses derivatives having a tetrahydronaphthyl structure that has an inhibitory effect on TrkA. However, the derivative described in Patent Document 5 is a urea derivative having a pyrazole ring, and there is no disclosure of compound (1) of the present invention.

PRIOR ART DOCUMENTS

Patent Documents

Patent Document 1: WO 2015/175788 brochure
Patent Document 2: WO 2015/039333 brochure
Patent Document 3: WO 2014/078378 brochure
Patent Document 4: WO 2014/078325 brochure
Patent Document 5: WO 2014/078454 brochure

Non-Patent Documents

Non-Patent Document 1: Current Opinion in Neurobiology, Vol. 11, pp. 272-280, 2001
Non-Patent Document 2: Journal of Pain Research, Vol. 9, pp. 373-383, 2016
Non-Patent Document 3: Journal of Neurochemistry, Vol. 124, pp. 276-289, 2013
Non-Patent Document 4: Cell, Volume 76, 1001-1011, 1994
Non-Patent Document 5: The FASEB Journal, Vol. 8, pp. 738-744, 1994
Non-Patent Document 6: Arthritis Research & Therapy, Vol. 18, p. 97, 2016
Non-Patent Document 7: Journal of Orthopaedic Research, Volume 33, pp. 1235-1241, 2015
Non-Patent Document 8: Pain, Vol. 138, pp. 47-60, 2008
Non-Patent Document 9: The Journal of Neuroscience, Vol. 27, pp. 8190-8201, 2007
Non-Patent Document 10: Biochimica et Biophysica Acta, Vol. 1866, pp. 37-50, 2016
Non-Patent Document 11: Cancer Discovery, Volume 5, pages 25-34, 2015
Non-Patent Document 12: Clinical & Translational Oncology, Volume 18, 599-607, 2016
Non-patent Document 13: Journal of Proteome Research, Volume 7, pp. 1932-1944, 2008
Non-patent Document 14: Nature Reviews Cancer, Volume 3, 203-216, 2003
Non-Patent Document 15: Journal of Alzheimer's Disease, Vol. 40, pp. 605-617, 2014
Non-Patent Document 16: Expert review of Respiratory Medicine, Volume 4, pp. 395-411, 2010

Non-Patent Document 17: Current Opinion in Pulmonary Medicine, Volume 7, pages 1-7, 2001

Non-Patent Document 18: Gut, Vol. 46, pp. 670-678, 2000

Non-Patent Document 19: Acta Dermato-Venereologica, Volume 95, 542-548, 2015

Non-Patent Document 20: Cytokine, Vol. 20, pp. 136-139, 2002

Non-Patent Document 21: Progress in Brain Research, Vol. 146, pp. 415-432, 2004

SUMMARY OF INVENTION

It is an object of the present invention to provide crystals of compound (1) suitable for the drug substance having the tropomyosin receptor kinase A (TrkA) inhibitory effect and useful as a preventive and/or therapeutic agent for pain, etc. In addition, by providing the crystals of compound (1) described above, it is possible to provide an excellent pharmaceutical composition.

The term "polymorphism" means the presence of two or more crystalline forms (crystalline structures) of a substance. Also, different crystalline forms of a particular substance are called "polymorphs". "Polymorphism" is generally reflected in the different atomic configurations in the crystal lattices of various polymorphs, either by altering conformations or by being influenced by intermolecular or intramolecular interactions (particularly, hydrogen bonding). On the other hand, the external shape of the material as a whole is referred to as a "morphology" or "crystalline morphology", which represents the external shape and the surface of the crystal, regardless of the internal structure. Crystals may exhibit a variety of crystalline morphologies depending on various conditions (such as growth rate, agitation method (speed, temperature), presence of impurities, etc.).

Since the various "polymorphism" of a substance may have different crystalline lattice energies, the polymorphism may exhibit different physical properties (such as shape, density, melting point, color, stability, solubility, dissolution rate, etc.) in solid states. The aforementioned physical properties may affect the stability, solubility, and bioavailability (such as drug absorption or action in vivo) of a particular polymorphism used in a pharmaceutical or pharmaceutical composition, as well as the storage life, formulation characteristics, and processing characteristics of a pharmaceutical product. Polymorphisms induce higher or lower biological activity compared to the intrinsic activity based on different rates of absorption.

The presence of multiple polymorphisms for a medicinal product can lead to "polymorphic rearrangement (or crystalline transition")", which means that a crystalline form changes to another crystalline form, namely crystalline structure changes, during the manufacturing or storage process of the medicinal product. If one polymorphism shows higher thermodynamic stability than another polymorphism, in some cases, the former should be selected than the latter for preparation of formulation. Therefore, one of the problems is to confirm the thermodynamic stability and select a more favorable polymorphism.

As a result of intensive research by the inventors of the present invention in order to solve the above problem, the compound (1) was successfully crystallized and four morphology of the compound (1) were found (the four morphology described herein are hereinafter referred to as Type I crystal, Type III crystal, Type V crystal and Type VI crystal, and Type I crystal is referred to as Form I, Type III crystal are referred to as Form III, and Type V crystal are referred to as Form V, and Type VI crystal are referred to as Form VI).

Furthermore, it was found that the four morphology of the compound (1) (Type I crystal, Type III crystal, Type V crystal, and Type VI crystal) have clearly different physical properties and can be expected as a raw material for pharmaceutical products, and the present invention has been completed.

The compound (1) of the present invention is a compound which has a tropomyosin receptor kinase A (TrkA) inhibitory effect regardless of the crystalline form of types I, III, V and VI, and has an improvement effect on diseases in which TrkA is involved (for example, pain, etc.).

Regardless of the crystalline forms of Type I, III, V and VI, pharmaceutical compositions containing the compound (1) of the present invention as an active ingredient are expected as prevention and/or therapeutic agents for diseases involving TrkA.

It can be understood that the type I crystal, the type III crystal, the type V crystal and the type VI crystal of the compound (1) of the present invention are the compounds having the TrkA inhibitory effect and are useful as pharmaceutical.

It is expected that the type I crystal, the type III crystal, the type V crystal, and the type VI crystal of the compound (1) of the present invention may be sufficient as raw materials for pharmaceutical products.

The type I crystal, the type III crystal, the type V crystal and the type VI crystal of the compound (1) of the present invention can provide superior pharmaceutical compositions.

DESCRIPTION OF EMBODIMENTS

The present invention relates to type I or type V crystal of 1-((1R,2R)-2-hydroxy-4,4-dimethyl-1,2,3,4-tetrahydronaphthalen-1-yl)-3-(5-methyl-6-(2-methylpyrimidin-5- yl)-2-phenylpyridin-3-yl)urea (compound (1)), a method of producing such crystal, and a pharmaceutical composition containing such crystal.

The present invention also relates to type III or type VI crystal of compound (1), method of producing the crystal, and pharmaceutical compositions containing the crystal.

The present invention includes the following embodiments [1] to [41].

Herein, the crystal described in any of the following embodiments [1] to [20] may be referred to as "crystal of 1-((1R,2R)-2-hydroxy-4,4-dimethyl-1,2,3,4-tetrahydronaphthalen-1-yl)-3-(5-methyl-6-(2-methylpyrimidin-5-yl)-2-phenylpyridin-3-yl)urea of the invention," "crystal of compound (1)" or "crystal of the invention."

Crystal described in any of embodiments [1] through [6] may be referred to as "type I crystal of the present invention."

Crystal described in any of embodiments [7] to [11] may be referred to as "type III crystal of the present invention."

Crystal described in any of embodiments [12] to [17] may be referred to as "type V crystal of the present invention."

Crystal described in any of the embodiments [18] to [20] may be referred to as "type VI crystal of the present invention."

[1] A first embodiment of the present invention is a type I crystal of 1-((1R,2R)-2-hydroxy-4,4-dimethyl-1,2,3,4-tetrahydronaphthalen-1-yl)-3-(5-methyl-6-(2-methylpyrimidin-5-yl)-2-phenylpyridin-3-yl)urea having characteristic peaks at least at diffraction angles (2θ) of 9.2±0.2, 11.2±0.2, 12.9±0.2, 18.0±0.2, 18.4±0.2, 21.3±0.2, 23.5±0.2, 24.0±0.2, 24.6±0.2, and 25.7±0.2 (°) in x-ray powder diffraction.

Figure 1:
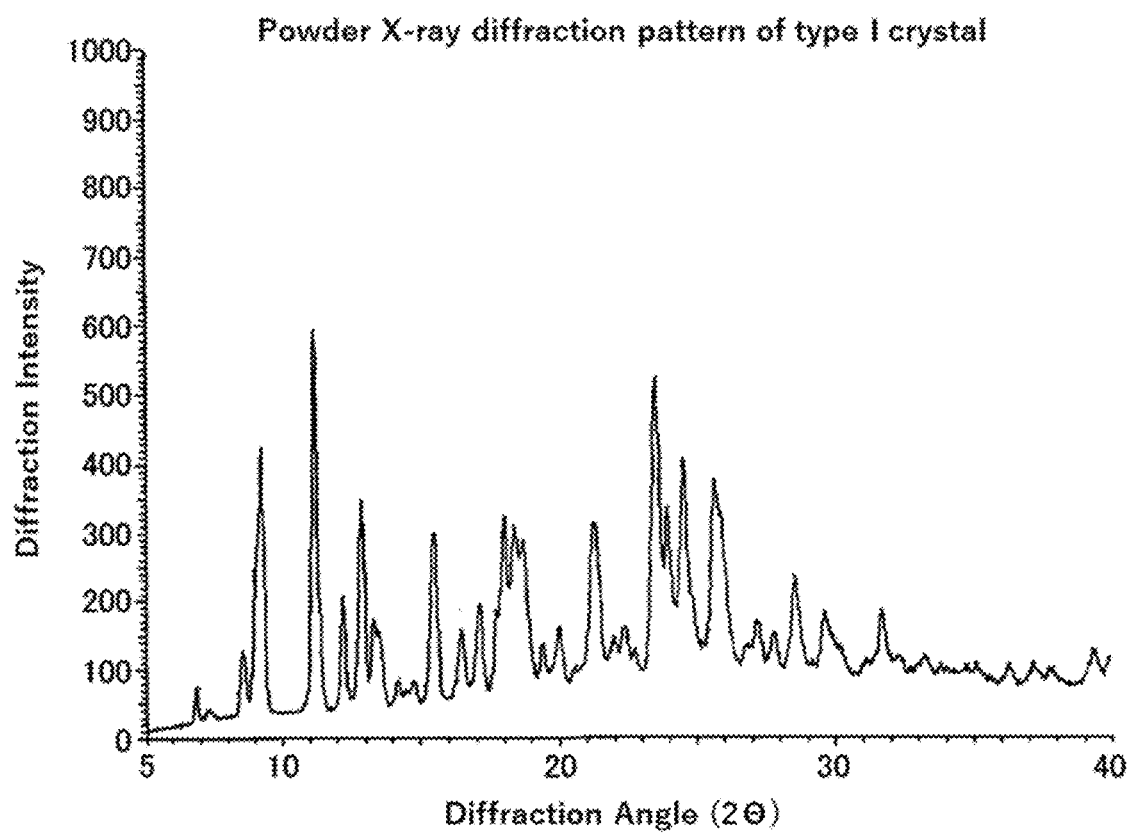
FIG. 1 is a powder X-ray diffraction pattern of the type I crystal of the compound (1) in Example 2.

[2] A second embodiment of the present invention is a type I crystal of 1-((1R,2R)-2-hydroxy-4,4-dimethyl-1,2,3,4-tetrahydronaphthalen-1-yl)-3-(5-methyl-6-(2-methylpyrimidin-5-yl)-2-phenylpyridin-3-yl) urea, characterized by an x-ray powder diffraction pattern shown in FIG. 1, wherein an error of ±0.2 (°) in diffraction angle (2θ) is allowed for each characteristic peaks of the x-ray powder diffraction pattern.

[3] A third embodiment of the present invention is a type I crystal of 1-((1R,2R)-2-hydroxy-4,4-dimethyl-1,2,3,4-tetrahydronaphthalen-1-yl)-3-(5-methyl-6-(2-methylpyrimidin-5-yl)-2-phenylpyridin-3-yl) urea, having diffraction angles (2θ) and relative intensities (%) of x-ray powder diffraction shown in Table 2.

Figure 2:
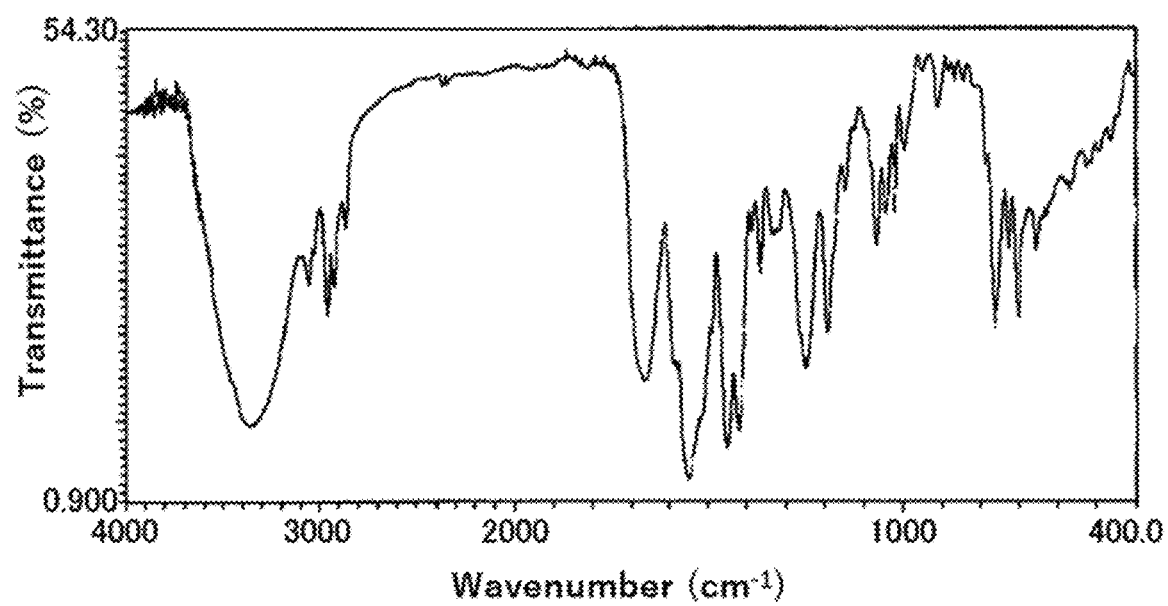
FIG. 2 is FT-IR spectral data of the type I crystal of the compound (1) in Example 2.

[4] A fourth embodiment of the present invention is a type I crystal of 1-((1R,2R)-2-hydroxy-4,4-dimethyl-1,2,3,4-tetrahydronaphthalen-1-yl)-3-(5-methyl-6-(2-methylpyrimidin-5-yl)-2-phenylpyridin-3-yl) urea, characterized by data values (cm$^{-1}$) shown in the FT-IR spectral data shown in FIG. 2; and preferably a type I crystal described in any one of the above [1] to [3], and characterized by data values (cm$^{-1}$) shown in the FT-IR spectral data shown in FIG. 2.

[5] A fifth embodiment of the present invention is a type I crystal of 1-((1R,2R)-2-hydroxy-4,4-dimethyl-1,2,3,4-tetrahydronaphthalen-1-yl)-3-(5-methyl-6-(2-methylpyrimidin-5-yl)-2-phenylpyridin-3-yl)urea, having an extrapolated melting point onset temperature of 131° C. in differential scanning calorimetry measurement (DSC measurement).

[6] A sixth embodiment of the present invention is the type I crystal as described in any one of the aforementioned embodiments [1] to [5], having a columnar crystal form.

[7] A seventh embodiment of the present invention is a type III crystal of 1-((1R,2R)-2-hydroxy-4,4-dimethyl-1,2,3,4-tetrahydronaphthalen-1-yl)-3-(5-methyl-6-(2-methylpyrimidin-5-yl)-2-phenylpyridin-3-yl) urea having characteristic peaks at least at diffraction angles (2θ) of 6.8±0.2, 10.3±0.2, 14.3±0.2, 15.3±0.2, 17.6±0.2, 19.7±0.2, 20.9±0.2, 21.6±0.2, 22.3±0.2, and 22.6±0.2 (°) in x-ray powder diffraction.

Figure 3:
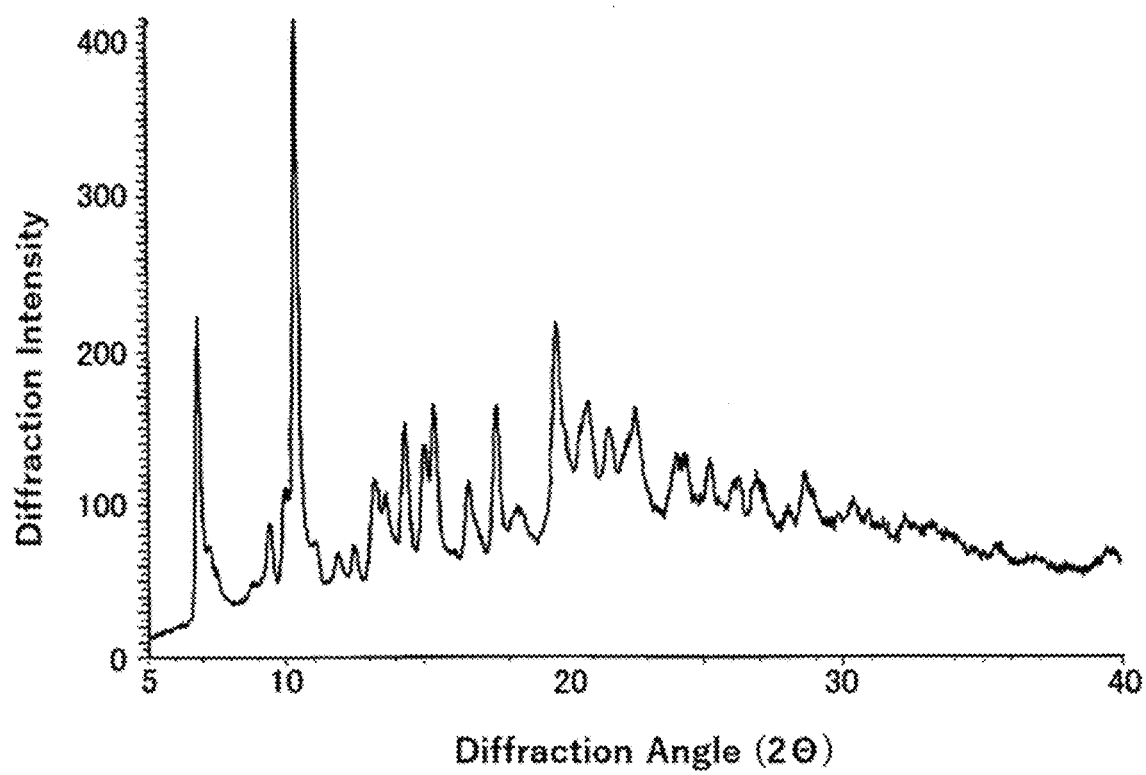
FIG. 3 is a powder X-ray diffraction pattern of the type III crystal of the compound (1) in Example 3.

[8] An eighth embodiment of the present invention is a type III crystal of 1-((1R,2R)-2-hydroxy-4,4-dimethyl-1,2,3,4-tetrahydronaphthalen-1-yl)-3-(5-methyl-6-(2-methylpyrimidin-5-yl)-2-phenylpyridin-3-yl) urea, characterized by an x-ray powder diffraction pattern shown in FIG. 3, wherein an error of ±0.2 (°) in diffraction angle (2θ) is allowed for each characteristic peaks of the x-ray powder diffraction pattern.

[9] A ninth embodiment of the present invention is a type III crystal of 1-((1R,2R)-2-hydroxy-4,4-dimethyl-1,2,3,4-tetrahydronaphthalen-1-yl)-3-(5-methyl-6-(2-methylpyrimidin-5-yl)-2-phenylpyridin-3-yl)urea, having diffraction angles (2θ) and relative intensities (%) of x-ray powder diffraction shown in Table 3.

Figure 4:
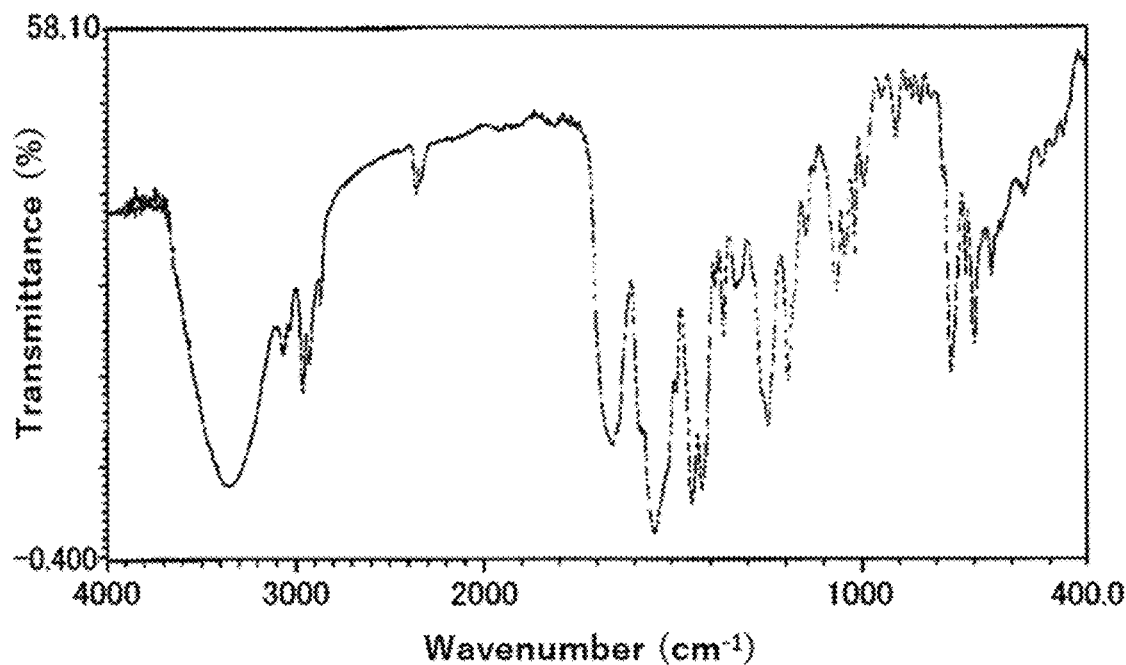
FIG. 4 is FT-IR spectral data of the type III crystal of the compound (1) in Example 3.

[10] A tenth embodiment of the present invention is a type III crystal of 1-((1R,2R)-2-hydroxy-4,4-dimethyl-1,2,3,4-tetrahydronaphthalen-1-yl)-3-(5-methyl-6-(2-methylpyrimidin-5-yl)-2-phenylpyridin-3-yl)urea, characterized by data values (cm$^{-1}$) shown in the FT-IR spectral data shown in FIG. 4; and preferably a type III crystal described in any one of the above [7] to [9], and characterized by data values (cm$^{-1}$) shown in the FT-IR spectral data shown in FIG. 4.

[11] An eleventh embodiment of the present invention is a type III crystal of 1-((1R, 2R)-2-hydroxy-4,4-dimethyl-1,2,3,4-tetrahydronaphthalen-1-yl)-3-(5-methyl-6-(2-methylpyrimidin-5-yl)-2-phenylpyridin-3-yl)urea, having an extrapolated melting point onset temperature of 121° C. in differential scanning calorimetry measurement (DSC measurement).

[12] A twelfth embodiment of the present invention is a type V crystal of 1-((1R,2R)-2-hydroxy-4,4-dimethyl-1,2,3,4-tetrahydronaphthalen-1-yl)-3-(5-methyl-6-(2-methylpyrimidin-5-yl)-2-phenylpyridin-3-yl) urea having characteristic peaks at least at diffraction angles (2θ) of 7.2±0.2, 10.8±0.2, 11.9±0.2, 14.5±0.2, 18.8±0.2, 22.3±0.2, 23.9±0.2, 24.2±0.2, 26.0±0.2 and 27.9±0.2 (°) in x-ray powder diffraction.

Figure 5:
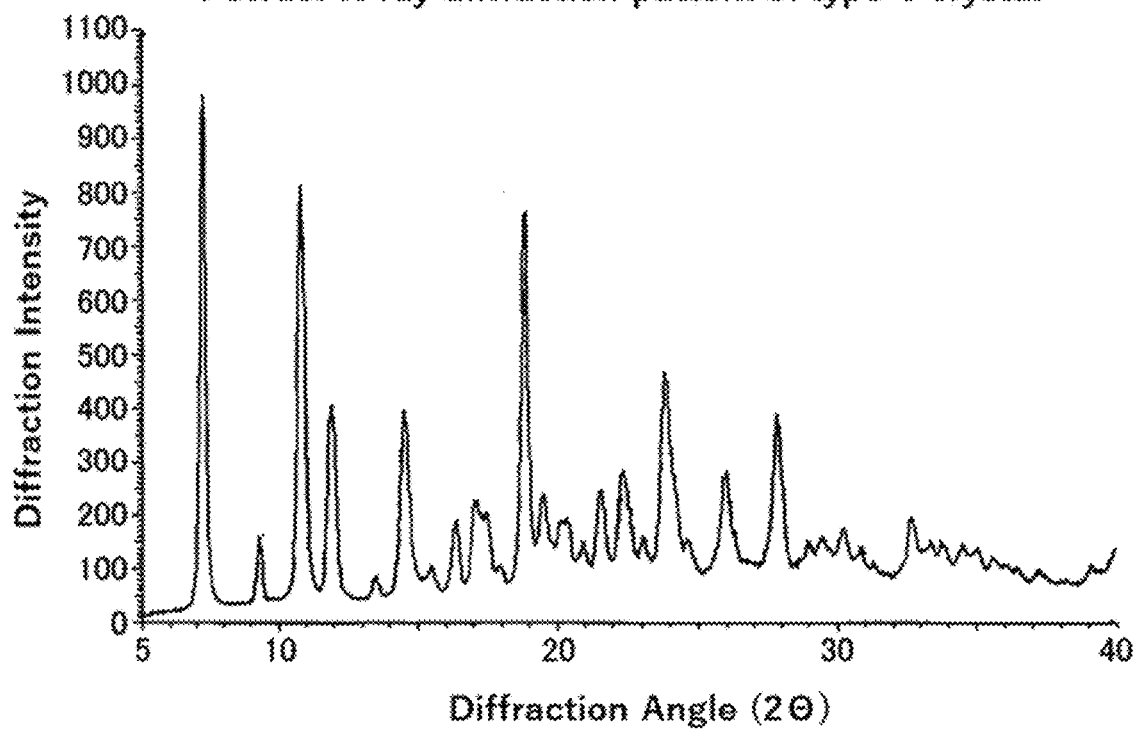
FIG. 5 is a powder X-ray diffraction pattern of the type V crystal of the compound (1) in Example 4.

[13] A thirteenth embodiment of the present invention is a type V crystal of 1-((1R,2R)-2-hydroxy-4,4-dimethyl-1,2,3,4-tetrahydronaphthalen-1-yl)-3-(5-methyl-6-(2-methylpyrimidin-5-yl)-2-phenylpyridin-3-yl) urea, characterized by an x-ray powder diffraction pattern shown in FIG. 5, wherein an error of ±0.2 (°) in diffraction angle (2θ) is allowed for each characteristic peaks of the x-ray powder diffraction pattern.

[14] A fourteenth embodiment of the present invention is a type V crystal of 1-((1R,2R)-2-hydroxy-4,4-dimethyl-1,2,3,4-tetrahydronaphthalen-1-yl)-3-(5-methyl-6-(2-methylpyrimidin-5-yl)-2-phenylpyridin-3-yl)urea, having diffraction angles (2θ) and relative intensities (%) of x-ray powder diffraction shown in Table 4.

Figure 6:
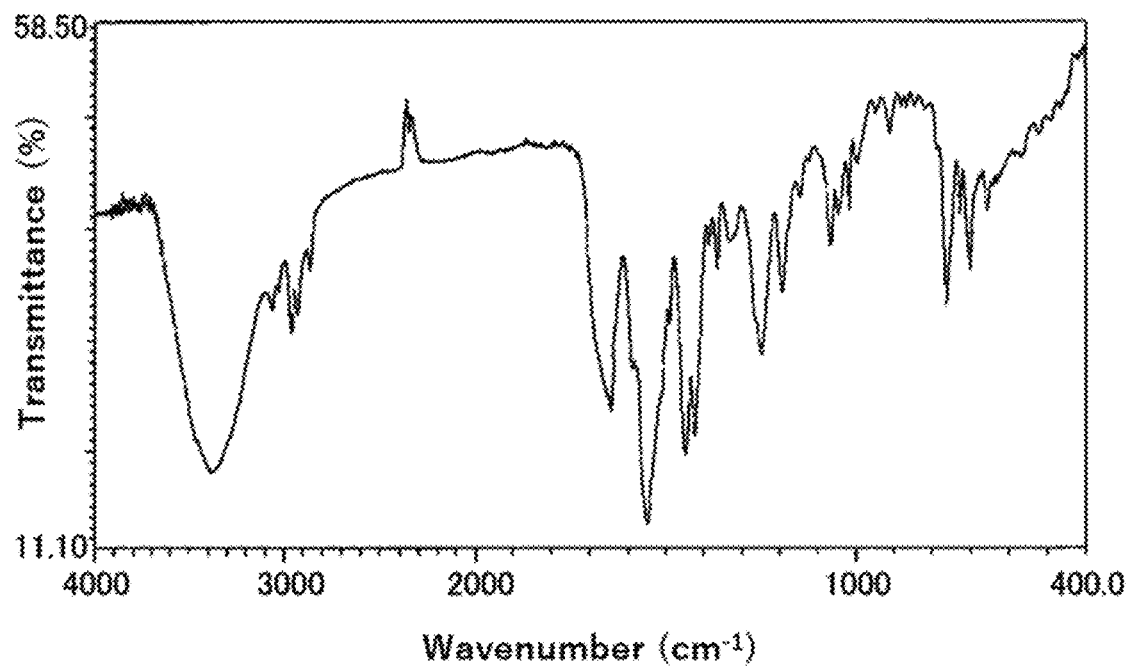
FIG. 6 is FT-IR spectral data of the type V crystal of the compound (1) in Example 4.

[15] A fifteenth embodiment of the present invention is a type III crystal of 1-((1R,2R)-2-hydroxy-4,4-dimethyl-1,2,3,4-tetrahydronaphthalen-1-yl)-3-(5-methyl-6-(2-methylpyrimidin-5-yl)-2-phenylpyridin-3-yl)urea, characterized by data values (cm$^{-1}$) shown in the FT-IR spectral data shown in FIG. 6; and preferably a type V crystal described in any one of the aforementioned embodiments [12] to [14], and characterized by data values (cm$^{-1}$) shown in the FT-IR spectral data shown in FIG. 6.

[16] A sixteenth embodiment of the present invention is a type V crystal of 1-((1R,2R)-2-hydroxy-4,4-dimethyl-1,2,3,4-tetrahydronaphthalen-1-yl)-3-(5-methyl-6-(2-methylpyrimidin-5-yl)-2-phenylpyridin-3-yl)urea, having an extrapolated melting point onset temperature of 149° C. in differential scanning calorimetry measurement (DSC measurement).

[17] A seventeenth embodiment of the present invention is the type V crystal as described in one of the aforementioned embodiments [12] to [16], having a columnar crystal form.

[18] An eighteenth embodiment of the present invention is a type VI crystal of 1-((1R,2R)-2-hydroxy-4,4-dimethyl-1,2,3,4-tetrahydronaphthalen-1-yl)-3-(5-methyl-6-(2-methylpyrimidin-5-yl)-2-phenylpyridin-3-yl) urea having characteristic peaks at least at diffraction angles (2θ) of 6.9±0.2, 9.2±0.2, 11.1±0.2, 13.3±0.2, 18.5±0.2, 19.0±0.2, 22.3±0.2, 22.8±0.2, 23.4±0.2, and 24.2±0.2 (°) in x-ray powder diffraction.

Figure 7:
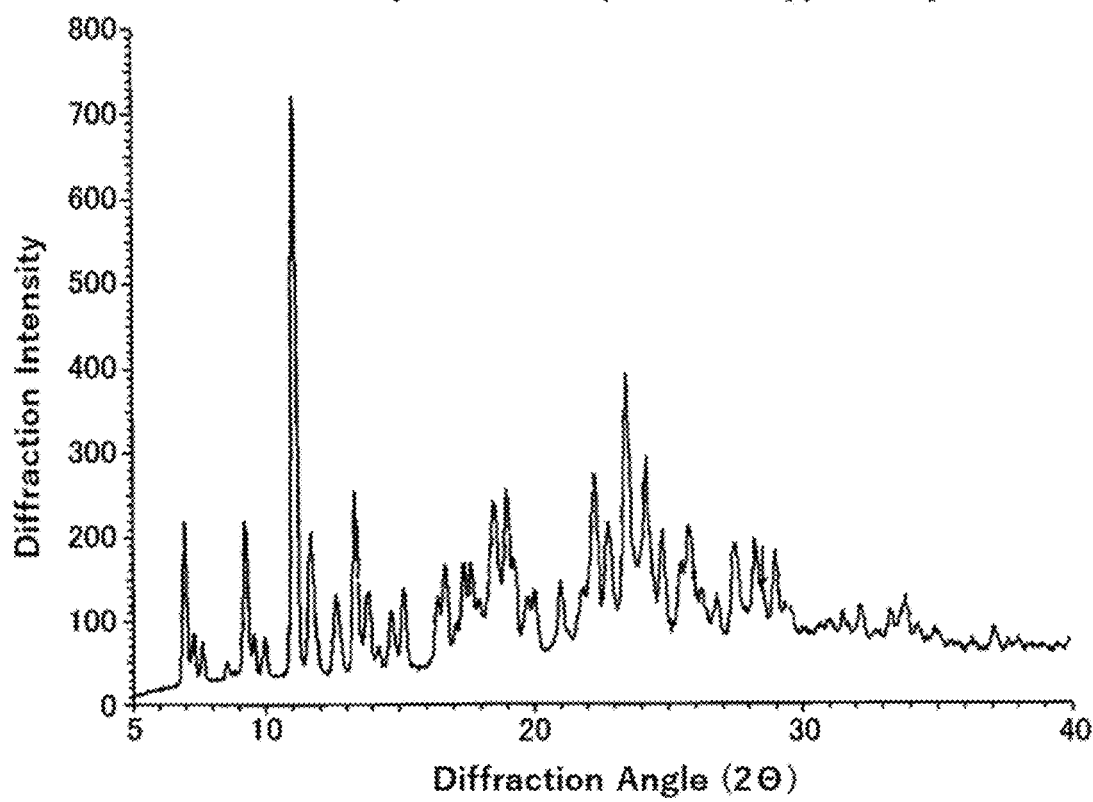
FIG. 7 is a powder X-ray diffraction pattern of the type VI crystal of the compound (1) in Example 5.

[19] A nineteenth embodiment of the present invention is a type VI crystal of 1-((1R,2R)-2-hydroxy-4,4-dimethyl-1,2,3,4-tetrahydronaphthalen-1-yl)-3-(5-methyl-6-(2-methylpyrimidin-5-yl)-2-phenylpyridin-3-yl) urea, characterized by an x-ray powder diffraction pattern shown in FIG. 7, wherein an error of ±0.2 (°) in diffraction angle (2θ) is allowed for each characteristic peaks of the x-ray powder diffraction pattern.

[20] A twentieth embodiment of the present invention is a type VI crystal of 1-((1R,2R)-2-hydroxy-4,4-dimethyl-1,2,3,4-tetrahydronaphthalen-1-yl)-3-(5-methyl-6-(2-methylpyrimidin-5-yl)-2-phenylpyridin-3-yl)urea, having diffraction angles (2θ) and relative intensities (%) of x-ray powder diffraction shown in Table 5.

[21] A twenty-first embodiment of the present invention is a method for producing a type I crystal of 1-((1R,2R)-2-hydroxy-4,4-dimethyl-1,2,3,4-tetrahydronaphthalen-1-yl)-3-(5-methyl-6-(2-methylpyrimidin-5-yl)-2-phenylpyridin-3-yl)urea as described in any one of the aforementioned embodiments [1] to [6], the method comprising a step of suspending 1-((1R,2R)-2-hydroxy-4,4-dimethyl-1,2,3,4-tetrahydronaphthalen-1-yl)-3-(5-methyl-6-(2-methylpyrimidin-5-yl)-2-phenylpyridin-3-yl) urea with a mixed solvents of alcohol solvents and water;

a step of dissolving the resulting mixed solution under heating at temperature below the boiling point of the solvent described above, (e.g., 50 to 90° C., preferably 60 to 80° C., more preferably 70±5° C.) and stirring (e.g., for 0.1 to 12 hours, preferably 20 minutes to 6 hours, and more preferably 30 to 60 minutes);

a step of stirring the dissolved mixed solution at the heating temperature described above (e.g., for 0.1 to 12 hours, preferably 20 minutes to 6 hours, and more preferably 30 minutes to 60 minutes);

and then a step of cooling the mixed solution with stirring to room temperature (e.g., for 1 to 48 hours, preferably 2 to 24 hours, more preferably 5 to 18 hours) to obtain the crystal.

[21-1] The alcohol solvents in the aforementioned embodiment [21] is preferably methanol, ethanol, or 2-propanol; more preferably methanol or ethanol.

[21-2] The mixing ratio in a mixed solvent of an alcohol solvent and water in the preparation described in the aforementioned embodiment [21] or [21-1] can be appropriately selected within a range of 4:1 to 1:1 (volume: volume, v/v). More specifically, for example, ethanol:water=4:1, 3:1, 2:1, or 7:3 or the ratio therebetween. The mixing solvent of this ratio is prepared and used in an amount to be dissolved as appropriate.

[21-3] In the method according to any one or more of the aforementioned embodiments [21] to [21-2], it is preferable that the crystal obtained by filtration be washed with a mixture solvent of an alcohol solvent and water having a mixture ratio of 1:4 (volume: volume, v/v) and/or with water, and then dried under reduced pressure.

[21-4] In the method according to any one or more of the aforementioned embodiments [21] to [21-3], it is more preferable that the obtained crystal be added to a mixture solvent, in which the mixing ratio of an alcohol solvent: water is 1:9 (volume: volume, v/v), stirred at 60 to 80° C. for 30 to 60 minutes, and then allowed to cool naturally to room temperature.

[22] A twenty-second embodiment of the present invention is a method for producing the type III crystal of 1-((1R,2R)-2-hydroxy-4,4-dimethyl-1,2,3,4-tetrahydronaphthalen-1-yl)-3-(5-methyl-6-(2-methylpyrimidin-5-yl)-2-phenylpyridin-3-yl)urea as described in any one of the aforementioned embodiments [7] to [11], the method comprising a step of suspending 1-((1R,2R)-2-hydroxy-4,4-dimethyl-1,2,3,4-tetrahydronaphthalen-1-yl)-3-(5-methyl-6-(2-methylpyrimidin-5-yl)-2-phenylpyridin-3-yl)urea in an ether solvent;

a step of stirring the resulting mixture for about 1 day, preferably 1 to 60 hours, preferably 6 to 48 hours, further preferably 12 to 36 hours, and then filtering the precipitated crystal.

[22-1] Example of the ether solvent in the aforementioned embodiment [22] includes diethyl ether, dimethoxyethane, tert-butyl methyl ether (MTBE), tetrahydrofuran or 1,4-dioxane etc; preferably tert-butyl methyl ether (MTBE).

[22-2] In the aforementioned embodiment [22], it is preferable to further comprise the steps of (1) further suspending in the same or a different solvent as above, and (2) stirring at room temperature for about 4 days, preferably for about 1 to 10 days, more preferably for 2 to 8 days, and even more preferably for 3 to 7 days.

[23] A twenty-third embodiment of the present invention is a method for producing the type V crystal of 1-((1R,2R)-2-hydroxy-4,4-dimethyl-1,2,3,4-tetrahydronaphthalen-1-yl)-3-(5-methyl-6-(2-methylpyrimidin-5-yl)-2-phenylpyridin-3-yl) urea as described in any one of the aforementioned embodiments [12] to [17], the method comprising a step of suspending the type I crystal (the aforementioned embodiments [1] to [6]) of 14(1R,2R)-2-hydroxy-4,4-dimethyl-1,2,3,4-tetrahydronaphthalen-1-yl)-3-(5-methyl-6-(2-methylpyrimidin-5-yl)-2-phenylpyridin-3-yl)urea with a mixed solvents of acetone and hydrocarbon solvents;

and a step of stirring the resulting mixed solution at room temperature (e.g., for 0.1 to 24 hours, preferably 30 minutes to 12 hours, more preferably about 1 hour±30 minutes, more preferably 1 hour).

[23-1] Example of the hydrocarbon solvents in the aforementioned embodiment [23] includes n-hexane and n-heptane, and preferably n-heptane.

[23-2] In the preparing method of the aforementioned embodiment [23] or [23-1], the mixing ratio in a mixed solvent of acetone and hydrocarbon solvents can be appropriately selected within a range of 3:1 to 1:1 (volume: volume, v/v). More specifically, for example, acetone:n-heptane=3:1, 2:1, or 1:1 or the like, preferably 1:1.

[23-3] In the aforementioned embodiment [23], it is preferable to further comprise the step of adding to the stirred solution the same or different mixture solvent as above, and then filtering off the precipitated crystal.

[24] A twenty-fourth embodiment of the present invention is a method for producing the type VI crystal of 1-((1R,2R)-

2-hydroxy-4,4-dimethyl-1,2,3,4-tetrahydronaphthalen-1-yl)-3-(5-methyl-6-(2-methylpyrimidin-5-yl)-2-phenylpyridin-3-yl)urea as described in any one of the aforementioned embodiments [18] to [20], the method comprising a step of suspending 1-((1R,2R)-2-hydroxy-4,4-dimethyl-1,2,3,4-tetrahydronaphthalen-1-yl)-3-(5-methyl-6-(2-methylpyrimidin-5-yl)-2-phenylpyridin-3-yl)urea in a mixture solvent of alcohol (e.g., methanol, ethanol, 2-propanol, etc.) with water (7:3);

a step of dissolving the resulting mixture while stirring at, for example, 50 to 100° C., preferably 60 to 90° C., more preferably, 70 to 80° C., for, for example, 1 to 120 minutes, preferably 10 to 60 minutes, more preferably 20 to 40 minutes;

a step of cooling the dissolved solution naturally to room temperature (e.g., 0.1 to 120 minutes, preferably 1 to 60 minutes, and more preferably 10 to 30 minutes).

[24-1] In the aforementioned embodiment [24], it is preferable that the filtered and obtained crystal be washed with a mixture solvent of ethanol with water (7:3; volume: volume, v/v), and then dried under reduced pressure.

[24-2] In the aforementioned embodiment [24], it is preferable to further comprise the step of allowing to cool naturally, stirring for 1 to 48 hours (preferably 2 to 24 hours and more preferably 5 to 18 hours) at room temperature, and then obtaining the precipitated crystal.

[25] A twenty-fifth embodiment of the present invention is a pharmaceutical composition characterized by comprising the crystal as an active ingredient as described in any one of the aforementioned embodiments [1] to [20].

[25-1] The crystal in the aforementioned embodiment [25] is preferably the type I crystal described in any one of the aforementioned embodiments [1] to [6].

[25-2] The crystal in the aforementioned embodiment [25] is preferably the type V crystal described in any one of the aforementioned embodiments [12] to [17].

[26] A twenty-sixth embodiment of the present invention is a pharmaceutical composition for treating at least one disease selected from the group consisting of: pain (such as pain associated with osteoarthritis, rheumatoid arthritis, bone fracture, interstitial cystitis, chronic pancreatitis, and prostatitis; chronic low back pain; diabetic peripheral neuropathic pain; postoperative pain; pelvic pain; nociceptive pain such as cancer pain; neuropathic pain; acute pain; chronic pain; or inflammatory pain); cancer; inflammatory/inflammatory disease; allergic disease; skin disease; neurodegenerative disease; infection; Sjogren's syndrome; endometriosis; renal disease; osteoporosis; and the like, and the composition comprising the crystal of one or more of the embodiments [1] to [20] as an active ingredient in an effective amount.

[26-1] The crystal in the embodiment [26] are preferably the type I crystal described in any one of the embodiments [1] to [6].

[26-2] The crystal in the embodiment [26] are preferably the type V crystal described in any one of the embodiments [12] and [17].

As used herein, unless otherwise specified, the term "treating" as in the phrase "treating a disease" means recovering, alleviating or inhibiting one or more "diseases" or the progression of the disease.

As used herein, the term "prevention" means preventing the onset of a "disease" or any symptom associated with a "disease" depending on the condition of the patient. It also includes preventing a "disease" and reducing the severity of the "disease" or any precritical symptom thereof.

[27] The twenty-seventh embodiment of the present invention is a pharmaceutical composition for treating at least one of the diseases described in the embodiment [26], containing the crystal described in any one of the embodiments [1] to [20] as an active ingredient in an amount effective to inhibit TrkA.

[27-1] The crystal in the embodiment [27] are preferably the type I crystal described in any one of the embodiments [1] to [6].

[27-2] The crystal in the embodiment [27] are preferably the type V crystal described in any one of the embodiments [12] to [17].

[28] The twenty-eighth embodiment of the present invention is a pharmaceutical composition comprising the crystal as an active ingredient according to any one of the embodiments [1] to [20], which is TrkA inhibitor.

[28-1] The crystal in the embodiment [28] is preferably the type I crystal described in any one of the embodiments [1] to [6].

[28-2] The crystal in the embodiment [28] is preferably the type V crystal described in any one of embodiments [12] to [17].

[29] The twenty-ninth embodiment of the present invention is a prevention and/or therapeutic agent for a disease involving TrkA, comprising the crystal as an active ingredient described in any one of the embodiments [1] to [20].

Example of "diseases involving TrkA" includes, but is not limited to, pain (such as pain associated with osteoarthritis, rheumatoid arthritis, fracture, interstitial cystitis, chronic pancreatitis, and prostatitis; chronic low back pain; diabetic peripheral neuropathic pain; postoperative pain; pelvic pain; nociceptive pain such as cancer pain; neuropathic pain; acute pain; chronic pain; or inflammatory pain), cancer, inflammatory/inflammatory disease, allergic disease, skin disease, neurodegenerative disease, infection, Sjogren's syndrome, endometriosis, renal disease, and osteoporosis.

[29-1] An embodiment [29-1] of the present invention is a crystal as described in any one of the embodiments [1] to [20] for the prevention and/or treatment of the disease involving TrkA.

[29-2] The crystal in the embodiment [29] or [29-1] is preferably the type I crystal described in any one of the embodiments [1] to [6].

[29-3] The crystal in the embodiment [29] or [29-1] is preferably the type V crystal described in any one of the embodiments [12] to [17].

The term "pain" is characteristic of many traumatic and disease states. When substantial damage to body tissues through disease or trauma occurs, the characteristics of nociceptor activation are altered, which leads to hypersensitivity in the site of injury and in adjacent normal tissue thereto. Example of pain includes, but is not limited to, osteoarthritis pain, arthralgia, neuropathic pain, postoperative pain, low back pain, diabetic neuropathy, intraoperative pain, cancer pain, chemotherapy-induced pain, headache (including cluster headache, tension headache, and migraine pain), trigeminal nerve pain, herpes zoster pain, postherpetic nerve pain, carpal tunnel syndrome, inflammatory pain, pain from rheumatoid arthritis, colitis, pain from interstitial cystitis, visceral pain, pain from kidney stones, pain from gallstones, throat pain, fibromyalgia, chronic pain syndrome, optic pain, pain from stroke, pharyngeal pain, sunburn, radiculopathy, complex local pain syndrome, HIV sensory neuropathy, central nervous pain syndrome, multiple sclerosis pain, Parkinson's disease pain, spinal cord injury pain, menstrual pain, tooth pain, pain from bone metastases, pain from endometriosis, pain from uterine fibroids, nociceptive pain, hyperalgesia, and temporomandibular joint pain.

The term "acute pain" is attributed to disease, inflammation, or tissue damage as defined by the International Pain Society. This type of pain generally occurs suddenly, e.g., after trauma or surgery, and may be accompanied by anxiety or stress, and is limited to a certain period and severity. In some cases, acute pain can become chronic.

The term "chronic pain" is widely believed to represent the disease itself, as defined by the International Pain Society. Chronic pain can be exacerbated by environmental and psychological factors. Chronic pain generally lasts more than 3 months and lasts longer than acute pain, and is resistant to most medical therapies. Chronic pain often causes serious problems because it can cause serious problems for patients. Chronic pain includes: cancer pain (pain arising from a tumor), visceral pain (e.g., visceral pain arising from pancreatic cancer and/or metastasis in the abdomen), and somatic pain (e.g., due to one or more of bone cancer, metastasis in bone, postoperative pain, sarcoma, cancer of connective tissue, cancer of bone tissue, cancer of bone marrow hematopoietic cells, multiple myeloma, leukemia, primary or secondary bone cancer).

The term "inflammatory pain" means pain resulting from inflammation. Inflammatory pain often manifests as increased sensitivity to mechanical stimuli (mechanical hyperalgesia or tenderness). For example, inflammatory pain depends on a condition selected from the group consisting of: burns, sunburns, arthritis, colitis, carditis, dermatitis, myositis, neuritis, mucositis, urethritis, cystitis, gastritis, pneumonia, and collagen vascular disease.

The term "neuropathic pain" means pain resulting from a condition or event that causes nerve damage. The term "neuropathy" means a disease process that causes damage to the nerve. "Causalgia" means chronic pain after nerve injury. "Heteralgia" refers to a condition in which a person feels pain, in response to a usually painless stimulus, such as a gentle touch.

"Neuropathic pain" is caused from conditions selected from, for example, causalgia, diabetes mellitus, collagen vascular disease, trigeminal neuralgia, spinal cord injury, brain stem injury, thalamic pain syndrome, complex regional pain syndrome type I/reflex sympathetic dystrophy, Fabry syndrome, small fibroneuropathy, cancer, cancer chemotherapy, chronic alcoholism, stroke, abscess, demyelinating disease, viral infection, antiviral therapy, AIDS, and AIDS therapy.

"Neuropathic pain" is caused from a factor selected from, e.g., trauma, surgery, amputation, toxin, chemotherapy and the like.

The term "Nociceptive pain" is elicited by severe stimuli that can cause tissue damage or injury. Painful afferent fibers are activated by nociceptor impulses at the site of injury, and then sensitize the spinal cord at their terminal positions. This is then relayed up the spinal tract to the brain where the pain is perceived. Activation of nociceptors leads to activation of two types of afferent fibers. Myelinated A-δ fibers transmit rapidly and provide a sharp stabbing sensation of pain, whereas unmyelinated C fibers transmit at a slower rate and transmit dull aching pain. Moderate to severe acute nociceptive pain has a prominent feature of bruising/sprain pain, postoperative pain (pain after any type of surgery), posttraumatic pain, burns, myocardial infarction, acute pancreatitis, and renal colic. In general, cancer-related acute pain syndromes are also due to therapeutic interactions such as chemotherapeutic toxicity, immunotherapy, hormonal therapy, and radiation therapy.

Moderate to severe acute nociceptive pain has a prominent feature of: cancer pain (e.g., bone pain, headache, facial pain, and visceral pain); cancer pain associated with cancer therapy (e.g., postchemotherapy syndrome, chronic postoperative pain syndrome, postirradiation syndrome); back pain that may be caused by abnormalities of disc or lumbar facet joint, sacroiliac joint, paravertebral muscle or posterior longitudinal band with prolapse or rupture, but not limited to these.

The term "cancer" means or represents a physiological condition in a mammal which is typically characterized by random cell proliferation. Specific example of "cancer" includes, but is not limited to, neuroblastoma, uterine body cancer, pleomorphic glioblastoma, cervical cancer, pancreatic cancer, colon cancer, rectal cancer, prostate cancer, melanoma, myeloma, thyroid cancer, lung cancer (small cell lung cancer, non-small cell lung cancer), encephaloma, esophageal cancer, kidney cancer, osteoma and blood cancer (chronic myeloid leukemia, acute lymphoblastic leukemia, Philadelphia chromosome positive acute lymphoblastic leukemia (Ph+ALL), acute myelogenous leukemia (AML), and chronic lymphocytic leukemia (CML)), squamous cell cancer, glioma, gastrointestinal cancer, ovarian cancer, liver cancer, gastric cancer, bladder cancer, hepatoma, breast cancer, head and neck cancer, germ cell tumor, childhood sarcoma, inus killers, and multiple myeloma.

Specific example of "inflammatory/inflammatory diseases" includes, but is not limited to, interstitial cystitis (IC), painful bladder syndrome (PBS), urinary incontinence, inflammatory cystitis, inflammatory bowel disease, ulcerative colitis, Crohn's disease, rheumatoid arthritis, joint swelling, asthma, atopic dermatitis, psoriasis, psoriatic arthritis, and systemic lupus erythematosus.

Specific example of "allergic diseases" includes, but is not limited to, asthma, atopic dermatitis, and rhinitis.

Specific example of "skin diseases" includes, but is not limited to, pruritus (including systemic skin pruritus, focal skin pruritus, and generalized skin pruritus).

Specific example of "renal diseases" includes, but is not limited to, diabetic nephropathy, renal fibrosis, and chronic kidney disease.

Specific example of "specific infections" includes, but is not limited to, cruise trypanosome infections.

Specific example of "neurodegenerative diseases" includes, but is not limited to, multiple sclerosis, Parkinson's disease, and Alzheimer's disease.

[30] A thirty embodiment of the present invention is a therapeutic agent for a disease involving TrkA, containing the crystal described in any one of the embodiments [1] to [20] as an active ingredient.

[30-1] The crystal in the embodiment [30] is preferably the type I crystal described in one of the embodiments [1] to [6].

[30-2] The crystal in the embodiment [30] is preferably the type V crystal as described in one of the embodiments [12] to [17].

[31] A thirty-first embodiment of the present invention is a preventive and/or therapeutic agent for pain (such as pain associated with osteoarthritis, rheumatoid arthritis, fracture, interstitial cystitis, chronic pancreatitis, and prostatitis; chronic low back pain; diabetic peripheral neuropathic pain; postoperative pain; pelvic pain; nociceptive pain such as cancer pain and the like; neuropathic pain; acute pain; chronic pain; or inflammatory pain), cancer, inflammatory/inflammatory disease, allergic disease, skin disease, neurodegenerative disease, infection, Sjogren's syndrome, endometriosis, renal disease or osteoporosis, and the agent containing the crystal as an active ingredient of any one of the embodiments [1] to [20].

Preferably, the embodiment [31] is a preventive and/or therapeutic agent for pain (such as pain associated with osteoarthritis, rheumatoid arthritis, bone fracture, interstitial cystitis, chronic pancreatitis, and prostatitis; chronic low back pain; diabetic peripheral neuropathic pain; postoperative pain; pelvic pain; nociceptive pain such as cancer pain, etc.; neuropathic pain; acute pain; chronic pain; or inflammatory pain), the agent containing the crystal as an active ingredient of any one of the embodiments [1] to [20].

[31-1] The embodiment [31-1] of the present invention is the crystal of any one of the embodiments [1] to [20] for the prevention and/or treatment of pain (such as pain associated with osteoarthritis, rheumatoid arthritis, fracture, interstitial cystitis, chronic pancreatitis, and prostatitis; chronic low back pain; diabetic peripheral neuropathic pain; postoperative pain; pelvic pain; nociceptive pain such as cancer pain and the like; neuropathic pain; acute pain; chronic pain; or inflammatory pain), cancer, inflammation/inflammatory disease, allergic disease, skin disease, neurodegenerative disease, infection, Sjogren's syndrome, endometriosis, renal disease and osteoporosis, and the like.

Preferably, the crystal according to any one of the embodiments [1] to [20] for the prevention and/or treatment of pain (such as pain associated with osteoarthritis, rheumatoid arthritis, fracture, interstitial cystitis, chronic pancreatitis, and prostatitis; chronic low back pain; diabetic peripheral neuropathic pain; postoperative pain; pelvic pain; nociceptive pain such as cancer pain; neuropathic pain; acute pain; chronic pain; or inflammatory pain).

[31-2] The crystal in the embodiment [31] or [31-1] is preferably the type I crystal described in one of the embodiments [1] to [6].

[31-3] The crystal in the embodiment [31] or [31-1] is preferably the type V crystal described in one of the embodiments [12] to [17].

[32] A thirty-second embodiment of the present invention is a therapeutic agent for at least one disease selected from the group consisting of the diseases described in the twenty-sixth embodiment of the present invention, comprising as an active ingredient the crystal described in any one of the embodiments [1] to [20].

[32-1] In the embodiments [32], the therapeutic agent for a pain disease comprising as an active ingredient the crystal according to any one of the embodiments [1] to [20] is preferable.

[32-2] The crystal in the embodiment [32] or [32-1] is preferably the type I crystal according to any one of the embodiments [1] to [6].

[32-3] The crystal in the embodiment [32] or [32-1] is preferably the type V crystal according to any one of the embodiments [12] to [17].

[33] A thirty-third embodiment of the present invention is a TrkA inhibitor comprising one or more of the crystals described in one of the embodiments [1] to [20].

[33-1] An embodiment [33-1] of the present invention is the crystal according to any one of the above embodiments [1] to [20] for TrkA inhibition.

[33-2] The crystal in the embodiment [33] or [33-1] is preferably the type I crystal described in one of the embodiments [1] to [6].

[33-3] The crystal in the embodiment [33] or [33-1] is preferably the type V crystal described in one of the embodiments [12] to [17].

[34] A thirty-fourth embodiment of the present invention is a use as a pharmaceutical composition of at least one of the crystal described in one of the embodiments [1] to [20].

[34-1] An embodiment [34-1] of the present invention is the use of the crystal described in any one of the embodiments [1] to [20], for preparation of pharmaceutical compositions.

[34-2] The crystal in the embodiment [34] or [34-1] is preferably the type I crystal described in any one of the embodiments [1] to [6].

[34-3] The crystal in the embodiment [34] or [34-1] is preferably the type V crystal described in any one of the embodiments [12] to [17].

[35] A thirty-fifth embodiment of the present invention is a use as TrkA inhibitor of at least one the crystal described in any one of the embodiments [1] to [20].

[35-1] An embodiment [35-1] of the present invention is a use of the crystal described in any one of the embodiments [1] to [20] for preparation of a TrkA inhibitor.

[35-2] The crystal in the embodiment [35] or [35-1] is preferably the type I crystal described in one of the embodiments [1] to [6].

[35-3] The crystal in the embodiment [35] or [35-1] is preferably the type V crystal described in one of the embodiments [12] to [17].

[36] A thirty-sixth embodiment of the present invention is a use of the crystal according to any one of the embodiments [1] to [20] in the preparation of a pharmaceutical composition.

[36-1] The crystal in the embodiment [36] is preferably the type I crystal described in any one of the embodiments [1] to [6].

[36-2] The crystal in the embodiment [36] is preferably the type V crystal described in any one of the embodiments [12] to [17].

[37] A thirty-seventh embodiment of the present invention is a use of the crystal according to any one of the embodiments [1] and [20] in the preparation of a TrkA inhibitor.

[37-1] The crystal in the embodiment [37] is preferably the type I crystal described in one of the embodiments [1] to [6].

[37-2] The crystal in the embodiment [37] is preferably the type V crystal described in one of the embodiments [12] to [17].

[38] A thirty-eighth embodiment of the present invention is a method for treating pain (such as pain associated with osteoarthritis, rheumatoid arthritis, fracture, interstitial cystitis, chronic pancreatitis, and prostatitis; chronic low back pain; diabetic peripheral neuropathic pain; postoperative pain; pelvic pain; nociceptive pain such as cancer pain; neuropathic pain; acute pain; chronic pain; or inflammatory pain), cancer, inflammation/inflammatory disease, allergic disease, skin disease, neurodegenerative disease, infection, Sjogren's syndrome, endometriosis, renal disease and osteoporosis; comprising administering to a subject in need of treatment at least one of the crystal described in any of the embodiments [1] to [20].

Preferably, the embodiment [38] is a method of treating pain (such as pain associated with osteoarthritis, rheumatoid arthritis, fracture, interstitial cystitis, chronic pancreatitis, and prostatitis; chronic low back pain; diabetic peripheral neuropathic pain; postoperative pain; pelvic pain; nociceptive pain such as cancer pain; neuropathic pain; acute pain; chronic pain; or inflammatory pain); more preferably pain (such as pain associated with osteoarthritis, rheumatoid arthritis, fracture, interstitial cystitis, chronic pancreatitis, and prostatitis; chronic low back pain; diabetic peripheral neuropathic pain; postoperative pain; pelvic pain; nociceptive pain such as cancer pain; neuropathic pain; acute pain; chronic pain; or inflammatory pain), and the method comprising administering to a subject in need of treatment of said disease at least one of the crystal described in any one of the embodiments [1] to [20].

[38-1] The crystal in the embodiment [38] is preferably the type I crystal described in one of the embodiments [1] to [6].

[38-2] The crystal in the embodiment [38] is preferably the type V crystal described in one of the embodiments [12] to [17].

Herein, the term "subject" includes non-human mammals such as dogs, cats, rats, mice, monkeys, cattle, horses, pigs, sheep, and the like, as well as humans.

As used herein, unless otherwise stated, the term "treatment" as in "treatment of a disease" means the recovery, alleviation, or inhibition of the progression of a "disease" or of one or more "diseases".

[39] A thirty-ninth embodiment of the present invention is a method for treating at least one disease selected from the group consisting of the diseases according to the twenty-sixth embodiment of the present invention; the method comprising administering to a subject in need of treatment of the disease the crystal according to any one of the embodiments [1] to [20] in an effective amount for treating the disease.

[39-1] The crystal in the embodiment [39] is preferably the type I crystal described in one of the embodiments [1] to [6].

[39-2] The crystal in the embodiment [39] is preferably the type V crystal described in one of the embodiments [12] to [17].

[40] A fortieth embodiment of the present invention is a method for treating at least one disease selected from the group consisting of the diseases according to the twenty-sixth embodiment of the present invention; the method comprising administering to a subject in need of treatment of the disease the crystal according to any one of the embodiments [1] to [20] in an amount effective to inhibit TrkA.

[40-1] The crystal in the embodiments [40] is preferably the type I crystal according to any one of the embodiments [1] to [6].

[40-2] The crystal in the embodiment [40] is preferably the type V crystal according to any one of the embodiments [12] to [17].

[41] A forty-first embodiment of the present invention is prevention and/or therapeutic agent according to the embodiment [29] or a method according to embodiment [38], in which the disease is osteoarthritis pain, arthralgia, neuropathic pain, postoperative pain, low back pain, diabetic neuropathy, intraoperative pain, cancer-induced pain, chemotherapy-induced pain, headache (including cluster headache, tension headache, migraine pain), trigeminal neuralgia, herpes zoster pain, postherpetic neuralgia, carpal tunnel syndrome, inflammatory pain, pain from rheumatoid arthritis, colitis, pain from interstitial cystitis, visceral pain, pain from kidney stone, pain from gallstone, throat sore, fibromyalgia, chronic pain syndrome, thalamic pain, pain from stroke, pharyngeal limb pain, sunburn, nerve root disorder, complex pain syndrome, HIV-sensory neuropathy, central nervous system pain syndrome, multiple sclerosis pain, Parkinson's disease pain, spinal cord injury pain, menstrual pain, tooth pain, pain from bone metastases, pain from endometriosis, pain from uterine fibroids, nociceptive pain, hyperalgesia, temporomandibular joint pain, neuroblastoma, uterine cancer, glioblastoma multiforme, cervical cancer, pancreatic cancer, colon cancer, rectal cancer, prostate cancer, melanoma, myeloma, thyroid cancer, lung cancer (small cell lung cancer, non-small cell lung cancer), encephaloma, esophageal cancer, kidney cancer, osteoma and blood cancer (chronic myelogenous leukemia, acute lymphoblastic leukemia, Philadelphia chromosome-positive acute lymphoblastic leukemia (Ph+ALL), acute myeloid leukemia (AML), and chronic lymphocytic leukemia (CML)), squamous cell cancer, glioma, gastrointestinal cancer, ovarian cancer, liver cancer, stomach cancer, bladder cancer, hepatoma, breast cancer, head and neck cancer, germ cell tumor, childhood sarcoma, paranasal sinus natural killer, multiple myeloma, interstitial cystitis (IC), painful bladder syndrome (PBS), urinary incontinence, inflammatory cystitis, inflammatory bowel disease, ulcerative colitis, Crohn's disease, systemic lupus erythematosus, rheumatoid arthritis, articular swelling, asthma, atopic dermatitis, psoriasis, arthritis with psoriasis, nasal inflammation, systemic cutaneous pruritus, focal cutaneous pruritus, generalized cutaneous pruritus, multiple sclerosis, Parkinson's disease, Alzheimer's disease, Cruise trypanosoma infection, Sjogren's syndrome, endometriosis, diabetic nephropathy, renal fibrosis, chronic kidney disease and osteoporosis.

[41-1] The crystal in the embodiment [41] is preferably the type I crystal described in one of the embodiments [1] to [6].

[41-2] The crystal in the embodiment [41] is preferably the type V crystal described in one of the embodiments [12] to [17].

The TrkA inhibitory effect of the crystal according to any one of the embodiments [1] to [20] of the present invention can be measured by an appropriately selected method, for example, the method in the Pharmacology Experiment 1 (Evaluation on binding activity against human TrkA protein) described below.

The crystal described in any one of the embodiments [1] to [20] of the present invention have excellent TrkA inhibitory activity as described in Pharmacology Experiment 1 (binding inhibitory effect against human TrkA).

Hereinafter, the present invention will be described in detail.

Any form of the crystal of 1-((1R,2R)-2-hydroxy-4,4-dimethyl-1,2,3,4-tetrahydronaphthalen-1-yl)-3-(5-methyl-6-(2-methylpyrimidin-5-yl)-2-phenylpyridin-3-yl)urea in the present invention may be a deuterated form.

In this specification, the method for analyzing crystal obtained can generally be a method for analyzing crystal by X-ray diffraction. Further example of method for determining crystal orientation includes mechanical or optical method (e.g., FT-Raman spectroscopy, solid NMR spectroscopy) and the like. Thermal analysis of crystal (Differential Scanning calorimetry (DSC), Thermal Gravimetric Analysis (TGA)), Infrared (IR) spectroscopy (KBr method, solution method) and the like) can also be used according to conventional procedure.

The spectral peaks obtained by the above-described analytical methods inevitably have constant measurement errors due to their nature. The scope of the crystal of the present invention also encompasses a crystal having spectral peaks with such errors.

For example, a particular crystal form sample has a main peak having the same diffraction angle (2θ) of a main peak of a different crystal form, but secondary peaks of the particular crystal form sample may show a difference in a powder X-ray diffraction pattern from the different crystal form. For diffraction angle (2θ) in powder X-ray diffraction, it means that an error of ±0.2 or ±0.1 is acceptable. In general, the diffraction angle (2θ) in powder X-ray diffraction can have an error within ±0.2°. Accordingly, the phrase "diffraction angle (2θ) of (about) X°" in the present invention means "diffraction angle (2θ) of ((X−0.2) to (X+0.2))°" unless otherwise stated. The present invention also includes a crystal in which the diffraction angle in powder X-ray diffraction is perfectly matched, as well as a crystal in which the diffraction angle is matched within an error margin within ±0.2°.

For the diffraction angle (2θ) of the powder X-ray diffraction herein, the term "characteristic peak" means a peak that exhibits maximum absorption at, for example, the diffraction angle (2θ) of the values listed in Tables 2, 3, 4 and 5. The relative intensity (%) for each diffraction angle (2θ) of powder X-ray diffraction may vary depending on the measurement condition since the crystal size and crystal direction may change strength of the X-ray at each peak in some cases, sometimes be undetectable.

For the infrared absorption ($cm^{-1}$) of the FT-IR spectrum, the error of "±0.2" or "±0.1" is acceptable.

As used herein, a crystal transition is a phenomenon in which the crystal structure changes when exceeding a certain temperature or pressure.

Example of the "crystal transition method" includes a method known in the art, for example: crystallization from a solution (e.g., concentration method, slow cooling method, reaction method (diffusion method and electrolysis method), water heat cultivation method, melting method, etc.); crystallization from a vapor (e.g., vaporization method (sealing method and airflow method), gas phase reaction method, chemical transport method); crystallization from a melt (e.g., normal freezing method (pull-up method, temperature gradient method, Bridgeman method), band melting method (zone leveling method, float zone method), special growth method (VLS method, liquid phase epitaxy method)); evaporation method (method of dissolving a crystal in a solvent and evaporating the solvent under atmospheric conditions after filtration); slurry method (method of adding crystals to a solvent to form a suspension so that excess solids remain, and collecting the solids after stirring at an atmospheric temperature or under heating or cooling); vacuum drying; grinding; pulverization; pressurization, etc.

A "columnar crystal" is a crystal being a polygonal such as triangular, square or pentagonal or circular in cross-section, and the crystal with a shape extending vertically from the cross-section. More specific shape of "column" includes, for example, cylindrical, triangular prism, square prism, hexagonal prism, octagonal prism, or similar shape to these.

The chemical purity of type I crystal, type III crystal, type V crystal, or type VI crystal according to the present invention is from about 95% to 100%, preferably from about 97% to 100%, and more preferably from about 99% to 100%.

A producing method of 1-((1R,2R)-2-hydroxy-4,4-dimethyl-1,2,3,4-tetrahydronaphthalen-1-yl)-3-(5-methyl-6-(2-methylpyrimidin-5-yl)-2-phenylpyridin-3-yl)urea (Compound (1))

Compound (1) may be prepared according to the method of Example 1 herein.

The structure of the compound (1) is shown below.

[Chemical Formula 1]

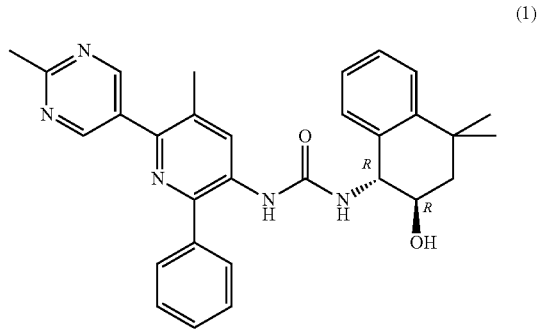

(1)

Coadministration Drug with the Crystal of the Present Invention or with Pharmaceutical Compositions Thereof The crystal of the present invention, or pharmaceutical compositions thereof, may be coadministered with other drug or agent in the common manner practiced in medical practice. Example of drug that may be coadministered or combined with the crystal of the present invention includes, for example, (A) drug for pain treatment, (B) drug for diseases where pain is likely to coexist, and the like.

Accordingly, according to another embodiment of the present invention, there is provided a pharmaceutical composition containing both of: the crystal of the compound (1); and one or more other drug or agent such as (A) drug for pain treatment, (B) drug for diseases where pain is likely to coexist and the like.

According to yet another embodiment of the present invention, there is provided a pharmaceutical composition comprising as an active ingredient at least one of a compound of formula (1), or a pharmaceutically acceptable salt or solvate thereof, in combination with other drug or agent such as (A) drug for pain treatment or (B) drug for diseases where pain is likely to coexist, and the like.

Example of (A) drug for pain treatment includes, for example:

(A1) Opioid agonists; (A2) pyrine antipyretic analgesics; (A3) non-pyridalyl antipyretic analgesics; (A4) non-steroidal anti-inflammatory drugs (NSAIDs); (A5) COX-2 selective inhibitors; (A6) drug for peripheral neuropathic pain and fibromyalgia; and (A7) descending pain inhibitory system; and the following drugs that have been diverted, and prescribed for neuropathic pain:

(A8) Anti-epileptics; (A9) Anti-depressants; (A10) Anti-arrhythmics; (A11) NMDA receptor antagonists; (A12) bisphosphonates; (A13) vanilloid receptor agonists; (A14) sodium channel modulators; (A15) fatty amide hydrolase (FAAH) inhibitory active compound; (A16) barbiturate sedatives; (A17) sedating benzodiazepines; (A18) H1 antagonists; (A19) 5-HT receptor agonists or antagonists; (A20) type 1 microsomal prostaglandin E synthase (mPGES-1) inhibitors; (A21) leukotriene B4 antagonists; (A22) α2-δ ligand; (A23) metabotropic glutamate subtype 1 receptor(mGluR1) antagonist; and (A24) prostaglandin E2 subtype 4 (EP4) antagonist.

Example of (B) drug for diseases where pain is likely to coexist includes an active agents against the TrkA pathway other than the compound (1) of the present invention, for example:

(B1) anti-diabetic drug such as: (i) PPARγ stimulants (agonists, inhibitors), (ii) insulin secretagogues, (iii) fast-acting insulin secretagogues, (iv) α-glucosidase inhibitors, and (v) insulin sensitizers (in particular, (a) PPARγ agonists, (b) PTP-1B inhibitors, (c) DPP-4 inhibitors, (d) GLP-1 and GLP-1 agonists, (e) 11β-HSD inhibitors, (f) GPR40 agonists, (g) GPR119 agonists, (h) GPR120 agonists), (vi) hepatic glucose neogenesis inhibitors, (vii) biguanides, (viii) insulin or insulin derivatives, (ix) α2 antagonists, and (x) SGLT2 inhibitors);

(B2) anti-obesity drug such as: (i) adrenergic β3 receptor agonists, (ii) CB-1 receptor antagonists, (iii) neuropeptide Y (NPY) receptor antagonists, (iv) feeding inhibitors, (v) lipase inhibitors, and (vi) peptide YY (PYY) receptor antagonists;

(B3) hyperlipidemia drug including cholesterol-lowering drug such as: (i) omega-3 fatty acids, (ii) HMG-CoA reductase inhibitors, (iii) HMG-CoA synthase inhibitors, (iv) cholesterol absorption inhibitors, (v) acyl-CoA cholesterol acyl transferase (ACAT) inhibitors, (vi) CETP inhibitors, (vii) squalene synthase inhibitors, (viii) antioxidants, (ix) PPARα agonists, (x) PPARδ agonists, (xi) LXR agonists, (xii) FXR agonists, (xiii) MTTP inhibitors, (xiv) squalene eposidase inhibitors, etc;

(B4) anti-hypertensives such as: (i) diuretics, (ii) calcium channel blockers, (iii) angiotensin-converting enzyme inhibitors (ACEI), (iv) angiotensin receptor blockers (ARB), (v) direct renin inhibitors, (vi) α-receptor blockers, (vii) β-receptor blockers, and (viii) α1β blockers;

(B5) disease-modifying antirheumatic drug (DMARDs); (B6) anticytokines; (B7) sex hormones or their derivatives; (B8) parathyroid hormone (PTH); (B9) $GABA_B$ receptor agonists; (B10) steroids; (B11) α-adrenergic agonists; (B12) α2-adrenergic receptor agonists;

(B13) sedatives; (B14) skeletal muscle relaxants; (B15) anti-convulsants; (B16) tachykinin (NK) antagonists (NK-3, NK-2, or NK-1 antagonists); (B17) muscarinic antagonists; (B18) coal tar analgesics; (B19) neuroleptics;

(B20) T2A receptor antagonists; (B21) 5-HT3 antagonists; (B22) cholinergic (nicotinic) analgesics; (B23) PDEV inhibitors; (B24) inducible nitric oxide synthase (iNOS) inhibitors; (B25) acetylcholinesterase inhibitors; (B26) 5-lipoxygenase inhibitors; (B27) anti-TNF therapy; (B28) antimetabolites and antifolate agents; (B29) specific kinase inhibitors;

(B30) anticonvulsants; (B31) calcitonin gene-related peptide receptor (CGRP) antagonists; (B32) tyrosine kinase targeted therapeutic agents; (B33) Ras-Raf-MEK-ERK pathway inhibitors; (B34) PI3K-Akt-mTOR-S6K pathway inhibitors; (B34) apoptosis regulators and signaling pathway inhibitors; (B35) cytotoxic chemotherapy agents;

(B36) angiogenesis-targeted therapies; (B37) immune-targeted agents; (B38) NGF-targeted biopharmaceuticals; and (B39) pan-Trk inhibitors.

When the compound (1) of the present invention is coadministered with an existing drug such as (A) and (B) above, the dosage of the existing drug can be reduced, and therefore the side effects of the existing drug can be reduced. Of course, the disease for the coadministration with coadministration drug is not limited to the disease described above, and the coadministration drug is not limited to the above listed drugs.

When the compound (1) of the present invention is coadministered with other drug such as those described in (A) and (B) above, separate formulations (or kit containing each) as well as a combination formulation may be used. Also, the separate formulations can be administered simultaneously or in a time-staggered manner.

The compound (1) of the present invention can be administered either as a single or multiple dose, or alone or in combination with a pharmaceutically acceptable carrier. Example of suitable pharmaceutical carrier includes: inert solid diluents or fillers, sterile aqueous solutions, and various organic solvents. The pharmaceutical composition formed thereby can then be readily administered in a variety of dosage formulations, such as tablets, powders, lozenges, liquid preparations, syrups, injectables, and the like. These pharmaceutical composition may optionally contain additional ingredients such as flavoring, binders, excipients and the like. Thus, the compound (1) of the present invention may be formulated for oral, buccal, nasal, parenteral (such as intravenous, intramuscular or subcutaneous), transdermal (e.g., patch), or rectal administration, or in dosage forms suitable for administration by inhalation or infusions.

Administration Embodiment for Coadministration

The administration embodiment for coadministration of the compound (1) of the present invention and the coadministration drug such as (A) and (B) are not particularly limited, as long as the compound (1) of the present invention and the coadministration drug are in combination upon administration. Example of such administration embodiment includes:

(1) Administration of a single combination formulation in which the compound (1) of the present invention and the coadministration drug are together formulated;

(2) Simultaneous coadministration by the same route of two separate formulations obtained by respectively formulating the compound (1) of the present invention and the coadministration drug;

(3) Staggered coadministration by the same route of two separate formulations obtained by respectively formulating the compound (1) of the present invention and the coadministration drug;

(4) Simultaneous coadministration by different routes of two separate formulations obtained by respectively formulating the compound (1) of the present invention and the coadministration drug, (5) Staggered coadministration by different routes of two separate formulations obtained by respectively formulating the compound (1) of the present invention and the coadministration drug.

For the staggered coadministration, the compound (1) of the present invention is administered and then the coadministration drug is administered; or in the reverse order).

These administration embodiments are hereafter abbreviated as "combined agents" of the present invention.

When using the combined agents of the present invention, the coadministration drug (A) or (B) and the compound (1) of the present invention can be coadministered simultaneously; after administering the coadministration drug, the compound (1) of the present invention can be administered: and also, after administering the compound (1) of the present invention, the coadministration drug can be administered. In a case of the time-staggered, the time difference therebetween depends on the active ingredient to be administered, the dosage form, and the method of administration. For example, in the case that the coadministration drug is administered in advance, the compound (1) of the present invention may be administered within 1 minute to 3 days, preferably within 10 minutes to 1 day, and more preferably within 15 minutes to 1 hour after administration of the coadministration drug. When the compound (1) of the present invention is administered in advance, the coadministration drug may be administered within 1 minute to 1 day, preferably within 10 minutes to 6 hours, and more preferably within 15 minutes to 1 hour after administration of the compound (1) of the present invention.

The dose of the coadministration drug can be adjusted on the basis of the dose used clinically, provided that the side effects are not of concern. In addition, the ratio of the compound of the invention (1) to the coadministration drug may be adjusted according to the subject of administration, route of administration, target disease, symptoms, combination, etc. When the compound (1) of the present invention is used in combination with the coadministration drug, the each dose can be reduced within a safe range considering the adverse effects of the drugs.

For example, when the subject to be administered is a human, the coadministration drug of 0.01 to 100 parts by weight, preferably 0.1 to 90 parts by weight, and more preferably 1 to 80 parts by weight may be administered for 1 part of the compound (1) of the present invention.

The combined agents of the present invention cause low toxicity, and can be formulated as pharmaceutical compositions, e.g., tablets (including dragees, film-coated tablets), powders, granules, capsules (including soft capsules), solutions, injectables, suppositories, sustained-release formulations, etc., through mixing the compound (1) of the present invention and/or the coadministration drug with a pharmaceutically acceptable carrier according to known methods. The formulation can be administered orally or parenterally (e.g., topically, rectally, intravenously, etc.).

Pharmaceutically acceptable carriers which may be used for preparation of the combined agents of the present invention can be similar to those used in the pharmaceutical compositions of the present invention.

The combination ratio of compound (1) of the present invention and the coadministration drug in the combined agents of the present invention can be adjusted depending on the subject of administration, the route of administration, the disease, etc.

Two or more coadministration drugs may be used in combination in an appropriate proportion.

The dose of coadministration drug may be appropriately adjusted based on the dose applied clinically. In addition, the ratio of the compound (1) of the present invention and the coadministration drug may be appropriately adjusted according to a subject to be administered, a route of administration, a subject disease, a symptom, a combination, etc. For example, when the administration subject is a human, the coadministration drug of 0.01 to 100 parts by weight may be administered for 1 part by mass of the compound (1) of the present invention.

For example, the content amount of the compound (1) in the combined agents of the present invention varies depending on the dosage form of the drug product, but is generally in the range of about 0.01% to 99.9% by weight, preferably in the range of about 0.1% to 50% by weight, and more preferably in the range of about 0.5% to about 20% by weight. The upper and lower limits of the numerical range may be arbitrarily combined with each other to provide a numerical range.

The content amount of the coadministration drug in the combined agents of the present invention varies depending on the dosage form of the formulation, but is in the range of about 0.01 to 99.9 wt %, preferably in the range of about 0.1 to about 50 wt %, and more preferably in the range of about 0.5 to about 20 wt % of the total drug product. The upper and lower limits of the numerical range may be arbitrarily combined with each other to provide a numerical range.

The content amount of an excipient, such as a carrier, in the combined agents of the present invention varies depending on the dosage form of the drug product, but is in the range of about 1 to 99.99 wt % and preferably in the range of about 10 to about 90 wt % relative to the total drug product. The upper and lower limits of the numerical range may be arbitrarily combined with each other to provide a numerical range.

The same amounts can be applied when the compound (1) of the present invention and the coadministration drug are formulated separately.

Since the dosage may vary under various conditions as noted above, less amount than the dosage described above can be sufficient or more amount than the dosage described above can be needed.

Pharmaceutical Composition of—Crystal of the Present Invention

The pharmaceutical composition of the crystal of the present invention comprises the crystal of 1-((1R,2R)-2-hydroxy-4,4-dimethyl-1,2,3,4-tetrahydronaphthalen-1-yl)-3-(5-methyl-6-(2-methylpyrimidin-5-yl)-2-phenylpyridin-3-yl)urea of the present invention, and are prepared in combination with a pharmaceutically acceptable additive. More specifically, the compound (1) of the present invention may be formulated in a variety of dosage forms in combination with:

excipients such as dextrose, lactose (monohydrate, spray-dried monohydrate, anhydrous, etc.), saccharose, sucrose, mannitol, Mannit, xylitol, sorbitol, crystalline cellulose, microcrystalline cellulose, silicic acid, starch, corn starch, potato starch, and calcium diphosphate dihydrate;

binders such as cellulose (hydroxypropyl cellulose (HPC), and hydroxypropyl methyl cellulose (HPMC)), crystalline cellulose, microcrystalline cellulose, gelatin, sugars (lactose, mannitol, sucrose, sorbitol, erythritol, and xylitol), starches (corn starch, potato starch), alpha starch, dextrin, and polyvinylpyrrolidone (PVP), macrogol, polyvinyl alcohol (PVA), polyethylene glycol, natural rubber, synthetic rubber, etc.;

lubricants such as magnesium stearate, calcium stearate, zinc stearate, sodium stearyl fumarate, mixtures of magnesium stearate and sodium lauryl sulfate, talc, carboxymethylcellulose, etc.;

disintegrants such as starches (corn starch, potato starch, starch, alpha-starch), carboxymethyl starch sodium, carmellose, carmellose calcium, croscarmellose sodium, crospopidone, sodium starch glycolate, sodium carboxymethyl cellulose, carboxymethyl cellulose calcium, polyvinylpyrrolidone, methyl cellulose, microcrystalline cellulose, lower alkyl substituted hydroxypropyl cellulose, sodium alginate, etc.;

surfactants such as sodium lauryl sulfate, polysorbate 80, etc.;

flow enhancers such as silicon dioxide, talc, etc.;

coatings such as cellulose (hydroxypropylcellulose (HPC), hydroxypropylmethylcellulose (HPMC), aminoalkylmethacrylate copolymer E, and methacrylate copolymer LD;

plasticizers such as triethyl citrate, and macrogol;

shielding agents such as titanium oxide;

colorants;

flavoring agents;

antiseptics such as benzalkonium chloride, and parahydroxybenzoate;

isotonicity agents such as glycerin, sodium chloride, calcium chloride, mannitol, and glucose;

pH modifiers such as sodium hydroxide, potassium hydroxide, sodium carbonate, hydrochloric acid, and sulfuric acid;

buffers such as phosphate buffer;

stabilizers such as sugars, sugar alcohols, and xanthan gum;

dispersants;

antioxidants such as ascorbic acid, butyl hydroxyanisole (BHA), propyl gallate, and dl-α-tocopherol;

buffering agent;

preservatives such as parabens, benzyl alcohol, and benzalkonium chloride;

aromatic agents such as vanillin, 1-menthol, rose oil, etc.;

dissolution aids such as polyoxyethylene hydrogenated castor oil, polysorbate 80, polyethylene glycol, phospholipid cholesterol, and triethanolamine;

absorption accelerators such as sodium glycolate, sodium edetate, sodium caprate, acylcarnitines, and limonene;

gelling agents;

suspending agents;

emulsifying agents; or suitable additives or solvents commonly used.

Example of various dosage forms includes: tablets, capsules, granules, powders, pills, aerosols, inhalants, ointments, patches, suppositories, injections, lozenges, solutions, spirits, suspensions, extracts, elixirs, and the like. The pharmaceutical compositions of the present invention may also be administered to a patient, for example, orally, subcutaneously, intramuscularly, intranasally, transdermally, intravenously, intraarterially, perineurally, epidurally, intradurally, intracerebrally, rectally, inhaled, and the like. The pharmaceutical compositions of the present invention are preferably suitable for oral administration.

The pharmaceutical composition of the present invention can be administered orally. Oral administration can mean orally taking and swallowing so that the compound enters the gastrointestinal tract; and also can mean oral or sublingual administration wherein the compound enters the bloodstream directly from the mouth. Example of formulation suitable for oral administration includes solid preparations or liquid preparations such as: tablet; capsule containing particulate, liquid, or powder; lozenge (including those containing liquid); chewing agent (chewing tablet); multiparticle and nanoparticle agent; solid preparation such as gel, solid solution, liposome, film (including mucosal adhesive), vaginal suppositorie, spray, and the like.

Example of liquid preparation includes suspension, solution, syrup, elixir, etc. These formulation can be used as a filler for soft or hard capsules, including carriers (e.g., water, ethanol, polyethylene glycol, propylene glycol, methylcellulose, or suitable oils, etc.) as well as one or more emulsifying and/or suspending agent. Liquid formulation can also be prepared by reconstitution from a solid such as sachet (pack or bag for granulation).

The pharmaceutical composition of the present invention can be administered directly into the bloodstream, muscle or viscera by injection such as catheterization techniques or infusions. Injections include intravenous, intraarterial, intraperitoneal, intrathecal, intracerebroventricular, intraurethral, intrasternal, intracranial, intramuscular, and subcutaneous administrations. Instruments such as needle syringes and needleless syringes should be used for injections. Direct administration by injection also includes pharmaceutical techniques such as, for example, preparation of injectable formulations by lyophilization.

Formulations for injection may be presented as unit dosage form, e.g., in ampoules or in multi-dose containers, with the addition of a preservative. These formulations may have the dosage forms such as suspensions, solutions or emulsions in oily or aqueous media, and may contain formulating agent such as suspending agent, stabilizing agent and/or dispersing agent. Alternatively, the active ingredient can be in powder form for reconstitution with a suitable medium, for example endotoxin-free water, prior to use.

In case a solution product is required, the solution product can be prepared by dissolving the isolated inclusion complex in water (or other aqueous medium) in an amount sufficient to produce a solution of the strength required for oral or parenteral administration to the patient. These compounds can be formulated in a fast dispersion dosage form (fddf) designed to release the active ingredient in the oral cavity. These formulations are often formulated using a rapid soluble gelatin-based matrix. These dosage forms are well known and can be used to deliver a various drugs. Most of fast dispersion dosage forms utilize gelatin as a carrier or as a structural forming agent. Typically, gelatin is used to impart sufficient strength to the dosage form to prevent breakage when removed from the package, and once in the mouth, gelatin allows the dosage form to be instantly dispersed. Alternatively, various starches may be used to obtain the same effect.

The pharmaceutical composition of the present invention can be administered topically on skin or mucous membranes, i.e., dermally or transdermally. Example of typical formulation includes gels, hydrogels, lotions, solutions, creams, ointments, sprays, dressings, foams, films, skin patches, wafers, implants, sponges, fibers, bandages and microemulsions. Liposomes can also be used.

The pharmaceutical composition of the present invention may be administered rectally or vaginally, for example, in dosage forms such as suppositories, pessaries or enemas. As a suppository base, for example, cocoa butter or other glycerides may be used to formulate rectal compositions such as suppositories or retention enemas.

The pharmaceutical composition of the present invention can also be administered directly to the eye or ear in the drop form of a micronized suspension or solution in an isotonic, pH-adjusted sterile saline. Example of other formulation suitable for eye and ear administration includes ointments, biodegradable (e.g., absorbable gel sponges, collagen) and non-biodegradable (e.g., silicone) implants, wafers, lenses, and particulate or vesicular agents such as niosomes or liposomes.

The pharmaceutical composition of the present invention can also be administered intranasally or by inhalation, for example, in dosage form of solution or suspension, in dosage form of dry powder from inhaler, or in dosage form of aerosol sprays. For the dosage form of solution or suspension, pump spray vessel which is pressed or pumped by the patient can be used. For aerosol sprays, pressurized container, pump, spray, atomizer or nebulizer can be used with or without suitable propellant or other suitable gas. For dry powder inhaler and aerosol, dose unit is determined by prefilled capsule, blister or pocket, or by system utilizing a dosing chamber supplied by mass measurement. The unit according to the present invention is typically configured to administer a constant amount or "puff" containing from 1 to 5000 μg of the compound or salt thereof. The total daily dose typically is in the range from 1 μg to 20 mg, and can be administered as a single dose or in divided doses.

For administration to a human patient, the total daily dose of the compound (1) of the present invention is determined according to the embodiment of administration, and is in the range of 0.005 mg to 200 mg, preferably in the range of 0.01 mg to 100 mg, and more preferably in the range of 0.1 mg to 50 mg. The total daily dose can be administered in single dose or divided doses. These doses are calculated based on an average human patient having a body weight of approximately 65 kg to 70 kg. The physician may determine the dosage for a subject (such as an infant and an elderly subject) whose weight is outside the above range.

The administration dosage for the therapy described above will vary depending upon the compound or salt used, the embodiment of administration, the desired treatment, and the disorder for which it is indicated. The dosage of the pharmaceutical composition of the present invention should preferably be set in accordance with the patient's age, body weight, type and degree of disease, route of administration and the like; and when administered orally, would normally be in the range of 0.05 to 100 mg/kg/day, preferably in the range of 0.1 to 10 mg/kg/day. Also, for parenteral administration, the dosage will vary greatly depending on the route of administration, but will normally be in the range of 0.005 to 10 mg/kg/day, preferably in the range of 0.01 to 1 mg/kg/day. It can be administered in once daily (single) dose to in several divided doses. The upper and lower limits of the numerical range may be arbitrarily combined with each other to provide a numerical range.

Pharmacology Experiments

Although the invention is specifically described with reference to the following experiments, the invention is not limited in any way by these experiments. The following pharmacology experiments 1 to 5 provide methods for evaluating the effectiveness of the crystal of the present invention.

(Pharmacology Experiment 1): Evaluation on Binding Activity Against Human TrkA Protein Measurements were made using TrkA LanthaScreen™ Eu Kinase Binding Assay (ThermoFisher SCIENTIFIC). Into 384 well plates (Corning), a 2.5 μL solution having each concentration of the test compound (1) diluted in Kinase buffer (ThermoFisher SCIENTIC) and a 2.5 μL having 15 nM TrkA enzyme (ThermoFisher SCIENTIFIC) were added. In addition, a 5 μL having 3 nM Eu-anti-His Tag antigen (ThermoFisher SCIENTIFIC) and 5 μL having 30 nM Kinase™ Tracer 236 (ThermoFisher SCIENTIFIC) were added, and allowed to react at room temperature for 60 minutes. After the reaction, the fluorescence ratio was calculated as the binding amount of the test compound (1) with TrkA enzyme, by measuring the fluorescence intensity (Emission wavelength 615 nm) and TR-FRET (Emission wavelength 665 nm) of Europium by the excitation wavelength of 340 nm using EnVision 2100 (PerkinElmer). The inhibitory activity ($IC_{50}$ value) of the test compound (1) was calculated as 0% fluorescence ratio of the wells to which solvent was added instead of the test compound (1) and as 100% fluorescence ratio of the wells to which no TrkA protein was added.

The inhibitory activity of each crystal of the test compound (1), which is 1-((1R,2R)-2-hydroxy-4,4-dimethyl-1,2,3,4-tetrahydronaphthalen-1-yl)-3-(5-methyl-6-(2-methylpyrimidin-5-yl)-2-phenylpyridin-3-yl)urea can be assessed by $IC_{50}$ value. Compound with $IC_{50}$ value of 50 nmol/L or less are shown in Table 1 as A (very high activity), those with $IC_{50}$ value greater than 50 nmol/L but 1000 nmol/L or less are shown as B (high activity), and those with $IC_{50}$ value greater than 1000 nmol/L are shown as C (low activity).

TABLE 1

| Test compound (1) | IC50 value |
|---|---|
| 1-((1R,2R)-2-hydroxy-4,4-dimethyl-1,2,3,4-tetrahydro-naphthalen-1-yl)-3-(5-methyl-6-(2-methylpyrimidin-5-yl)-2-phenylpyridin-3-yl) urea (Type III crystal) | A |

(Pharmacology Experiment 2): Evaluation on Inhibitory Activity in Human TrkA-Expressing Cells The inhibitory activity against TrkA kinase in cell lines was measured as an index of ligand-dependent increases in intracellular calcium concentrations in CHO-K1 cells (CellSenser™ TrkA-NFAT-bla CHO-K1 cells, ThermoFisher SCIENTIFIC) which stably express human TrkA.

The day before the assay, the cells were suspended in Opti-MEM™ 1 Reduced Serum Medium (ThermoFisher SCIENTIC) containing assay medium (0.5% inactivated Dialyzed FBS (ThermoFisher SCIENTIC), NEAA (ThermoFisher SCIENTIFIC), 1 mM Sodium Pyruvate (ThermoFisher SCIENTIC)), and seeded into 96 well clear bottom plates (Greiner) at a density of $4.0 \times 10^4$ cells/100 μL/well. On the day of the assay, a 100 μL of loading buffer containing 2.5 mM probenecid (FLIPR Calcium assay kit, molecular device) was added, and incubated for 1 hour at 37° C. under 5% $CO_2$. The test compound (1) pre-diluted with 20 mM HEPES/HESS containing 0.1% BSA (final concentration of DMSO: 0.1%) was added, and the resulting solution were set in an intracellular calcium concentration measurement system (FDSS 7000, Hamamatsu Photonics). NGF-β (Sigma Aldrich Japan) was added 5 minutes after the addition of the test compound (1) (final concentration: 30 ng/mL), and the intracellular calcium concentration was measured as a fluorescent signal. The inhibitory activity ($IC_{50}$ value) of the test compound was calculated as 0% fluorescent signal of the well to which solvent was added instead of test compound (1) and as 100% fluorescent signal of the well to which no NGF-β was added.

(Pharmacology Experiment 3): Inhibitory Effect on NGF-Induced Vascular Permeability Increase in Rats The inhibitory activity against TrkA in vivo was evaluated. Clipped back male Sprague-Dawley rats (CD(SD)IGS rats, Charles River, Japan) were orally administered test compound (1) dissolved or suspended in a solvent (dose volume: 5 mL/kg). Vehicle controls were treated orally with vehicle. 1 to 24 hours after administration, 1% Evans blue (Nacalai tesque) was administered intravenously into the tail vein under isoflurane anesthesia (dose volume: 3 mL/kg), immediately followed by intradermal administration of 300 ng/mL NGF (mouse 2.5s, Alomone) diluted with saline to two sites on the back and of saline to two sites on the back (dose volume: 50 µL/site). Ten minutes after intradermal injection, the administration skin sites (four sites) were cut off, and the skin samples were transferred to each well of a 24-well plate (Nikkei Corporation). Formamide (Wako Pure Chemical Industries, Ltd.) was added to the plates in 1.5 mL/well, covered, and incubated overnight at 37° C. A 200 µL of the formamide extract was transferred to a 96-well plate (Nunc), and the absorbance (wavelength: 620 nm) of Evans blue extracted into formamide was measured using SpectraMax (Molecular Device).

Concurrently, the absorbance of authentic preparations of Evans Blue diluted with formamide were also measured, and a calibration curve was prepared. The Evans blue concentration of each sample was calculated from the calibration curve and the absorbance of each sample.

The individual value was calculated by subtracting the mean value of the two sites receiving saline from the mean value of the two sites receiving NGF, among of the four site skin samples collected from the one individual. The inhibition rate of NGF-induced vascular hyperlucency in rats was calculated as 0% of the Evans blue concentration in the vehicle control group.

(Pharmacology Experiment 4): Analgesic Effect on Complete Freund's Adjuvant (CFA)-Induced Rat Model The analgesic effect of the test compound (1) was evaluated in a CFA-induced rat model.

(1) Preparation of CFA-Induced Rat Model

An emulsion was prepared by mixing equal amounts of CFA (Sigma Aldrich Japan) and saline, and a 100 µL thereof was administered to the right footpad of rats under isoflurane anesthesia using a 26-gauge needle. The normal control group received 100 µL of saline.

(2) Administration of the Test Compound (1) or Anti-NGF Antibody

The test compound (1) was dissolved or suspended in 0.5% methylcellulose (Wako Pure Chemical Industries, Ltd.) (dose volume: 5 mL/kg). Anti-NGF antibody as a positive control was dissolved and diluted with saline to prepare a solution of 2 mL/kg. The test compound (1) group was orally administered twice daily for 7 days from the day of administration of CFA. Anti-NGF antibody was administered intraperitoneally on the same day as CFA administration.

(3) Measurement of 50% Threshold (G)

Measurements were made 7 days after CFA administration. After calming the animals to the measurement environment for at least 1 hour, the footpads were stimulated with von Frey filaments according to the Dixon up-down method (Journal of Neuroscience Methods, Vol. 53, pp. 55-63, 1994), and then 50% threshold (g) was calculated by the following equation. Measurements were made in a blinded manner.

$$50\% \text{ threshold } (g) = (10^{[Xf+k\delta]}/10000)$$

Xf: Value of the filament last used
k: Tabular value
δ: Mean difference between filaments used (=0.224)

(Pharmacology Experiment 5): Pharmacokinetic Study

The compound of Example 2 (type I crystal) and the compound of Example 4 (type V crystal) described below were employed as compounds (1) of the present invention, and these crystals were administered orally to male Crl:CD (SD) rats aged 6-9 weeks at a single dose of 600 mg/kg (solvent for administration: 10 mL/kg of a 0.5 w/v % methylcellulose 400 solution), followed by blood sampling from the jugular vein after 0.25, 0.5, 1, 2, 4, 6, 8, and 24 hours. Plasma sample obtained by centrifugation of blood (12000×g, for 5 minutes, at 4° C.) was measured to determine plasma concentration of the test compound using high performance liquid chromatography/mass spectrometry. Similarly, concentrations of standard solutions containing the test compound at known concentrations (0.001, 0.002, 0.005, 0.01, 0.02, 0.05, 0.1, 0.2, 0.5, 1, 2, and 5 µg/mL) were measured. And then, the plasma concentration (µg/mL) of the compound (1) was calculated from the prepared calibration curve to obtain the maximum plasma concentration (Cmax (µg/mL)) and the area under the plasma concentration-time curve (AUC (µg·hr/mL)). Measurement conditions can be appropriately adjusted by a person skilled in the art.

The results of the compound of Example 2 (type I crystal) and the compound of Example 4 (type V crystal) are shown below.

<Maximum Plasma Concentration ($C_{max}$)>
Compound of Example 2 (type I crystal): 29.7 µg/mL
Compound of Example 4 (type V crystal): 26.9 µg/mL
<Area under Plasma Concentration (AUC)>
Compound of Example 2 (type I crystal): 561 µg·hr/mL
Compound of Example 4 (type V crystal): 473 µg·hr/mL These results indicate that the compound (1) of the present invention has an excellent TrkA inhibitory effect. In addition, the results of the pharmacology experiments 3 and 4 in rats showed no abnormalities in the safety test, indicating the low toxicity of the present invention. Furthermore, from the results of the pharmacology experiment 5, it was found that absorbability of the crystals of the compound (1) of the present invention was extremely high.

Accordingly, the compound (1) of the present invention is expected to be used as a TrkA inhibitor for the prevention and/or treatment of diseases involving TrkA, such as pain (pain associated with osteoarthritis, rheumatoid arthritis, fracture, interstitial cystitis, chronic pancreatitis, prostatitis; chronic low back pain; diabetic peripheral neuropathic pain; postoperative pain; pelvic pain; nociceptive pain such as cancer pain; neuropathic pain; acute pain; chronic pain; or inflammatory pain), cancer, inflammatory/inflammatory disease, allergic disease, skin disease, neurodegenerative disease, infection, Sjogren's syndrome, endometriosis, renal disease, and osteoporosis. Since their prevention and/or therapeutic use is not depended on crystalline form, any of the type I, III, V and VI crystals of the compound (1) are expected to have the use for the prevention and/or treatment of the above-mentioned diseases.

The type I, III, V, and VI crystals of the compound (1) of the present invention are expected to exhibit promising preventive or therapeutic effects on a variety of diseases in which TrkA is involved.

All references and publications herein are incorporated by reference in their entirety for any purpose whatsoever.

EXAMPLE

Next, Examples and Test Examples are given for the purpose of illustrating the present invention in more detail, but these examples are merely embodiments and are not intended to be limiting of the scope of invention, and may be varied without departing from the scope of the invention.

Nuclear magnetic resonance (NMR) spectra were determined using JEOL JNM-ECX400 FT-NMR (manufactured by Japan Electronics), JEOL JNM-ECX300 FT-NMR (manufactured by Japan Electronics), or Bruker Avance III 400 MHz NMR (manufactured by Bruker).

Liquid chromatography-mass spectrometry (LC-Mass) spectra were determined by the following methods:

[UPLC] [Method A] With Waters AQUITY UPLC system and CAPCELL Pak column (2.0 mm×50 mm, 3 μm) (manufactured by Shiseido), mobile phase of "Methanol:Trifluoroacetic acid aqueous solution (0.05%)" was used in gradient conditions of 5:95 (0 minutes), 95:5 (1.0 minutes), 95:5 (1.6 minutes) and 5:95 (2.0 minutes);

[LCMS] [Method B] With Waters FractionLynx MS system (manufactured by Waters) and SunFire column (4.6 mm×5 cm, 5 μm) (manufactured by Waters), mobile phase of "Acetonitrile:Acetic acid aqueous solution (0.05%)" was used in gradient conditions of 10:90 (0 minute), 100:0 (5.0 minutes), 100:0 (6.0 minutes) and 10:90 (7.0 minutes); or [Method C] mobile phase of "Acetonitrile:Trifluoroacetic acid aqueous solution (0.05%)" was used in gradient conditions of 10:90 (0 minutes), 100:0 (5.0 minutes), 100:0 (6.0 minutes) and 10:90 (7.0 minutes).

For the preparative separation system, gradient conditions modified depending on the compound was used. Optical resolution by supercritical fluid liquid chromatography (SFC) was performed using Waters SFC Prep15 System, SFC80q System and the corresponding chiral columns thereto. Optical purity analysis was performed using Waters SFC UPC2 and the corresponding chiral columns thereto. For LC-Mass, mass spectrometry with ESI (electrospray ionization) (MS-ESI) was used.

For the pattern of NMR signals in $^1$H-NMR data, "s" denotes singlet, "d" denotes doublet, "t" denotes triplet, "q" denotes quartet, "m" denotes multiplet, "br" denotes broad, "J" denotes coupling constant, "Hz" denotes Hertz, CDCl$_3$ denotes deuterated chloroform, DMSO-D6 denotes deuterated dimethyl sulfoxide, and CD3OD denotes deuterated methanol. Undetectable signals in $^1$H-NMR due to broadband, such as protons of hydroxyl groups (OH), amino groups (NH$_2$) and carboxyl groups (COOH), are not described in the data.

In the MS-ESI data in the table below, "M" denotes the molecular weight, "[M+H]$^+$" denotes the molecular ion peak. "A", "B", and "C" in the table mean "UPLC [Method A]," "LCMS [Method B]," and "LCMS [Method C]," respectively. MS-ESI means mass spectrometry with ESI.

As used herein, "room temperature" refers to a temperature of normally 1° C. to 30° C. (as defined in Japan Pharmacopeia), preferably 20° C.±15° C. (JIS Z 8703), and more preferably 15 to 25° C. In Examples of the specification, "room temperature" refers to 20° C.

For the crystallization process in Examples, commercial solvents were used without purification.

Powder X-ray diffraction analysis was made using D8 Discover with GADDS CS (manufactured by Bruker) according to the Bragg-Brentano method (under conditions of X-ray source: 40 kV, 40 mA, Wavelength: 1.5418 Å (CuKalpha), Camera length: 250 mm, temperature: room temperature, Phi Position: 0 degrees, Exposure time: 2 minutes, Theta 1: 7 degrees, Theta 2: 7 degrees).

FT-IR was measured according to the KBr method using FT-720 (manufactured by HORIBA). Micrographs were obtained using MT4300L (manufactured by Meiji Techno).

For differential scanning calorimetry (DSC), a differential scanning calorimeter DSC Q2000 (manufactured by TA instruments) was used to measure in temperature range of 40° C. to 300° C. at temperature increasing rate of 10° C. per minute. For thermogravimetric analysis (TGA), a differential scanning calorimeter TGA Q50 (manufactured by TA instruments) was used to measure in temperature range of 40° C. to 400° C. at temperature increasing rate of 10° C. per minute.

Here, the phrase "an extrapolated starting temperature of melting point" means the onset temperature of the peak of the melting point of the compound. For example, in FIG. 8 (DSC spectral data for type I crystal), a melting point peak is 137.47° C., and its onset temperature is 131.09° C., i.e., the extrapolated starting temperature of melting point is 131° C.

The extrapolated starting temperatures of melting point for each type of crystal is as follows.

TABLE A

Figure 8:
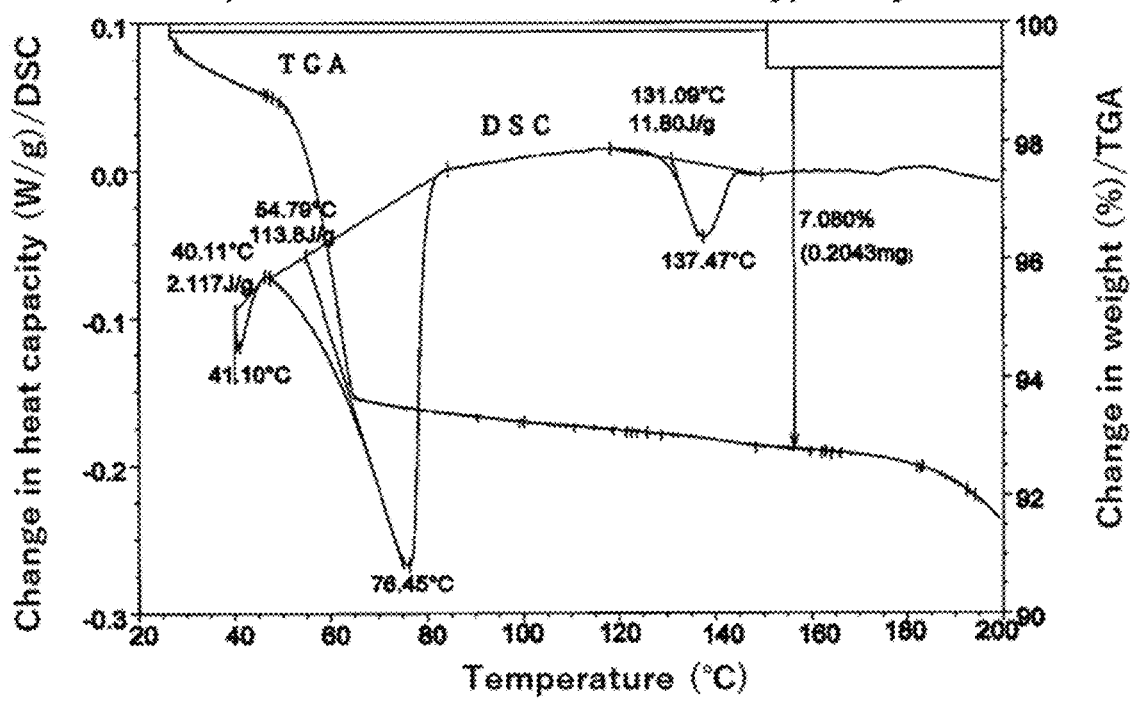
FIG. 8 is spectral data of DSC and TGA of the type I crystal of the compound (1) in Example 2.
Figure 10:
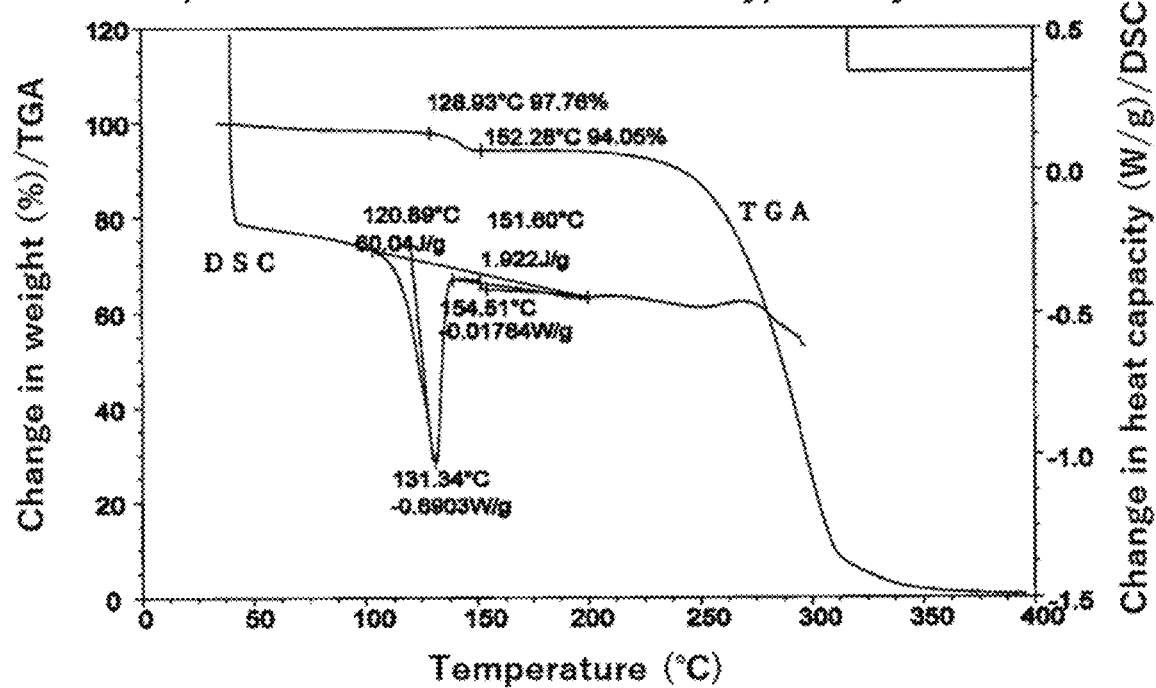
FIG. 10 is spectral data of DSC and TGA of the type III crystal of the compound (1) in Example 3.
Figure 11:
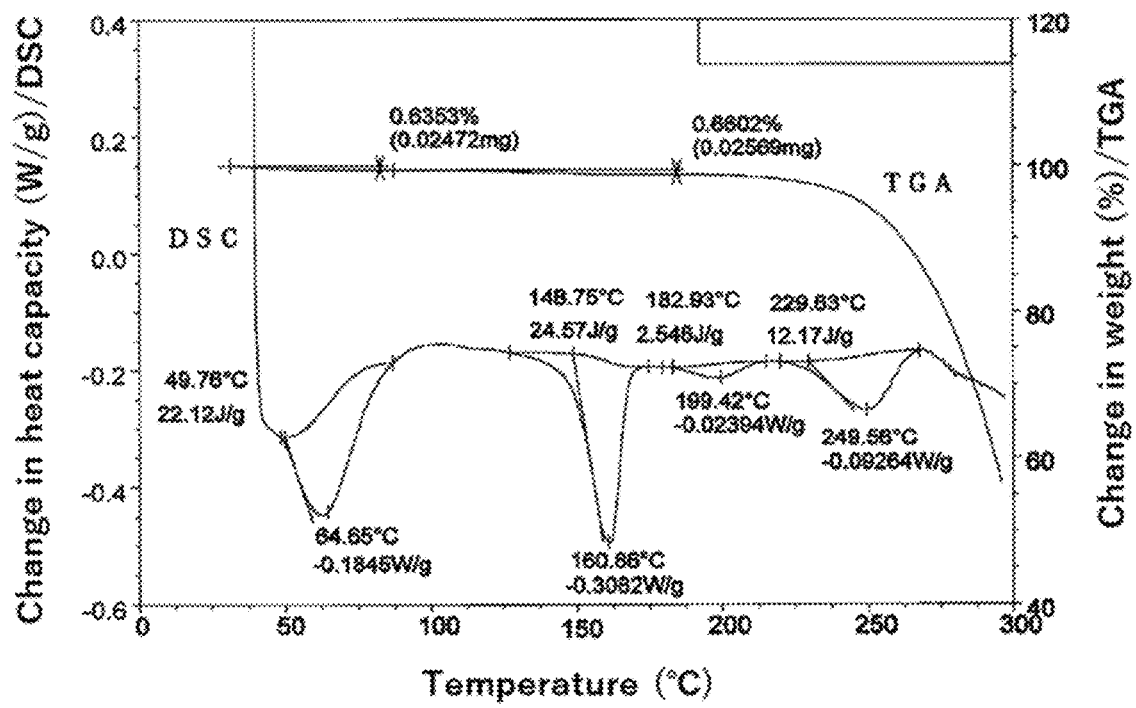
FIG. 11 is spectral data of DSC and TGA of the type V crystal of the compound (1) in Example 4.

| Crystalline morphology | FIG. | Extrapolated starting temperatures of melting point |
| --- | --- | --- |
| Type I crystal | FIG. 8 | 131° C. |
| Type III crystal | FIG. 10 | 121° C. |
| Type V crystal | FIG. 11 | 149° C. |

For the stability test, approximately 20 mg of the test sample was stored at 25° C./60% RH or at 40° C./75% RH in open or closed condition for 1 month using a small environmental tester SH-641 (manufactured by Espec), and changes in purity and in crystalline form were observed.

For purity measurement, equipment of Waters ACQUITY UPLC H-Class (manufactured by Waters) and column of Waters ACQUITY BEH C18 (particle diameter 1.7 μm, size 2.1×50 mm) are used. For the mobile phase, 10 mmol/L ammonium bicarbonate buffer pH 9.0 and acetonitrile were used; and the test sample solution at 100 μg/mL in the mixture solvent of THF (tetrahydrofuran):10 mmol/L ammonium bicarbonate buffer (20:80) was prepared.

Example 1

Synthesis of 1-((1R,2R)-2-hydroxy-4,4-dimethyl-1,2,3,4-tetrahydronaphthalen-1-yl)-3-(5-methyl-6-(2-methylpyrimidin-5-yl)-2-phenylpyridin-3-yl)urea (Example 1=Compound (1))

<Step 1> Synthesis of 5-methyl-2-phenylpyridin-3-amine (Example 1-1)

Commercially available 2-chloro-5-methyl-3-pyridinamine (CAS No. 34552-13-1) (1.0 g), phenylboronic acid (0.86 g) and tetrakis(triphenylphosphine)palladium (0.81 g) were added to a mixture solvent of ethanol (15 mL), toluene (35 mL) and 2N potassium carbonate aqueous solution (11 mL), and the mixture was stirred under a nitrogen atmosphere at 100° C. for 18 hours. After cooling, the resulting solution was separated by adding ethyl acetate and water, the organic layer was washed with brine, and dried over sodium sulfate. The solvent was evaporated under reduced pressure, and the residue was purified by silica gel column chromatography on silica gel (mobile phase: heptane/ethyl acetate 70:30 to 65:35 to 60:40) to obtain the title compound (1.2 g) as a colorless solid.

<Step 2> Synthesis of 6-bromo-5-methyl-2-phenylpyridine-3-amine (Examples 1-2)

N-bromosuccinimide (0.21 g) was added to a solution of the compound (0.19 g) obtained in <Step 1> of (Example 1) in N-methylpyrrolidone (2.0 mL), and the mixture was stirred at room temperature for 2 hours. Water (2.0 mL) was added to the resulting reaction mixture, and the mixture was extracted twice with tert-butyl methyl ether, then the organic layer was washed with water. The solvent was evaporated under reduced pressure, and the residue was purified by silica gel column chromatography (stationary phase: amino-silica gel, mobile phase: heptane/ethyl acetate 90:10 to 30:10) to obtain the title compound (0.20 g) as a brown solid.

<Step 3> Synthesis of 5-methyl-6-(2-methylpyrimidin-5-yl)-2-phenylpyridine-3-amine (Examples 1-3)

To a mixture solution of the compound (0.40 g) obtained in <Step 2> of (Example 1) in 1,2-dimethoxyethane (10 mL) and water (2.0 mL), 2-methyl-5-(4,4,5,5-tetramethyl-1,3,2-dioxaborolan-2-yl) pyrimidine (0.44 g), cesium carbonate (1.5 g) and dichloro[1,1'-bis(diphenylphosphino)ferrocene] palladium dichloromethane adduct (0.12 g) were added, and the mixture was stirred at 80° C. for 4 hours. After cooling, water was added to the resulting reaction mixture. The insoluble material was filtered off with celite pad and washed with ethyl acetate; and the organic layer was separated from the filtrate, washed successively with water and brine, and dried over sodium sulfate. The residue obtained by evaporation of the solvent under reduced pressure was purified by silica gel column chromatography (stationary phase: amino-silica gel, mobile phase: heptane/ethyl acetate=100:0 to 50:50) to obtain the title compound (0.31 g).

<Step 4> Synthesis of 2,2,2-trichloroethyl (5-methyl-6-(2-methylpyrimidin-5-yl)-2-phenylpyridin-3-yl) carbamate (Examples 1-4)

Pyridine (0.22 mL) and 2,2,2-trichloroethyl chloroformate (0.36 mL) were added to a solution of the compound (0.30 g) obtained in <Step 3> of (Example 1) in 1,2-dichloroethane (100 mL) at room temperature, and the mixture was stirred at the same temperature for 1 hour. Sodium bicarbonate aqueous solution was added to the resulting reaction mixture, and the mixture was extracted with ethyl acetate, then the organic layer was washed successively with water and brine, and dried over sodium sulfate. The solvent was evaporated under reduced pressure, and the residue was purified by silica gel column chromatography (stationary phase: amino-silica gel, mobile phase: heptane/ethyl acetate=2:1) to obtain the title compound (0.41 g) as a white solid.

<Step 5> Synthesis of 4,4-dimethyl-1,2,3,4-tetrahydronaphthalen-1-ol (Examples 1-5)

Sodium borohydride (0.24 g) was added in two fractions to a mixture of commercially available 4,4-dimethyl-3,4-dihydronaphthalen-1(2H)-one (CAS No. 2979-69-3) (1.0 g) in methanol (10 mL) under ice-water cooling, and the mixture was stirred at room temperature for 1 hour. Methanol was removed under reduced pressure, and 1N sodium hydroxide aqueous solution (30 mL) and ethyl acetate (40 mL) were added to the resulting residue, then the mixture was separated. The organic layer was washed with brine (25 mL), dried over sodium sulfate, then concentrated under reduced pressure to obtain the title compound (1.0 g) as a pale yellow oily product.

<Step 6> Synthesis of 1,1-dimethyl-1,2-dihydronaphthalene (Examples 1-6)

A mixture of the compound (1.0 g) obtained in <Step 5> of (Example 1) and p-toluenesulfonic acid monohydrate (0.05 g) in toluene (10 mL) was stirred at 90° C. for 1.5 hours. After cooling to room temperature, ethyl acetate (40 mL) and saturated sodium bicarbonate aqueous solution (30 mL) were added, and the resulting mixture was separated. The organic layer was washed with brine, dried over sodium sulfate, and concentrated under reduced pressure to obtain the title compound (0.86 g) as a yellow oily product.

<Step 7> Synthesis of 3,3-dimethyl-1a,2,3,7b-tetrahydronaphtho[1,2-b]oxylene (Examples 1-7)

An aqueous solution (0.60 mL) of potassium peroxymonosulfate (0.15 g) was added to a suspended mixture of the compound (30 mg) obtained in <Step 6> of (Example 1) and sodium bicarbonate (80 mg) in acetone (0.60 mL) under ice cooling. The resulting mixture was stirred at the same temperature for 1 hour and at room temperature for 16 hours. Then, ethyl acetate and saturated sodium bicarbonate aqueous solution were added to the reaction mixture, and the mixture was separated. The organic layer was washed successively with sodium thiosulfate aqueous solution and brine, then dried over sodium sulfate. The solvent was evaporated under reduced pressure, and the residue was purified by silica gel column chromatography (mobile phase: heptane/ethyl acetate=100:0 to 90:10) to obtain the title compound (24 mg) as a colorless oily product.

<Step 8> Synthesis of rac-(1RS,2RS)-1-amino-4,4-dimethyl-1,2,3,4-tetrahydronaphthalen-2-ol (Examples 1-8)

25% aqueous ammonia (1.0 mL) was added to a solution of the compound (30 mg) obtained in <Step 7> of (Example 1) in ethanol (0.070 mL). The resulting mixture was stirred in a sealed tube at 90° C. for 1 hour. After cooling, water was added to the reaction mixture, and the precipitated solid was collected and dried under reduced pressure to obtain the title compound (14 mg).

<Step 9> Synthesis of (1R,2R)-1-amino-4,4-dimethyl-1,2,3,4-tetrahydronaphthalen-2-ol (2S,3S)-2,3-dihydrosuccinate monohydrate (Examples 1-9)

D-(-)-tartaric acid (2.7 g) was added to a mixture of the compound (3.4 g) obtained in <Step 8> of (Example 1) in acetonitrile (74 mL) and water (19 mL) at room temperature. The resulting reaction mixture was stirred at 100° C. for 5 minutes, cooled to room temperature, and kept at the same temperature for 2 hours. The precipitated crystal was collected, washed with a pre-cooled mixture solvent of acetonitrile-water (4:1), and dried under reduced pressure to obtain the product (2.0 g). Acetonitrile-water (4:1) (25 mL) was added to this product, and the mixture was stirred at 100° C. for 10 minutes, cooled to room temperature, and kept for 1 hour at the same temperature so as to conduct recrystallization. The precipitated crystal was collected, washed with a pre-cooled mixture solvent of acetonitrile-water (4:1), and dried under reduced pressure to obtain the title compound (1.4 g) as a colorless solid.

<Step 10> Synthesis of 1-((1R,2R)-2-hydroxy-4,4-dimethyl-1,2,3,4-tetrahydronaphthalen-1-yl)-3-(5-methyl-6-(2-methylpyrimidin-5-yl)-2-phenylpyridin-3-yl)urea (Example 1=Compound (1))

The compound (76 mg) obtained in <Step 9> of (Example 1) and triethylamine (0.093 mL) were added to a solution of the compound (0.10 g) obtained in <Step 4> of (Example 1) in N-methyl pyrrolidone (0.50 mL), and the mixture was stirred at 40° C. for 18.5 hours. Water (3.0 mL) was added to the resulting reaction mixture, and the precipitate was collected and washed with water. The obtained crude product was suspended and triturated in a mixture solvent of heptane-isopropanol (9:1), collected, washed with a mixture of heptane-isopropanol (9:1), and then dried under reduced pressure to obtain the title compound (82 mg).

Structures of the intermediate compounds described above (Examples 1-1) to (Examples 1-9) and the final compound of (Example 1) are shown below. $^1$H-NMR data (no symbol: 400 MHz NMR, symbol "*": 300 MHz NMR) and LC-Mass data for the final compound of Example 1 are presented in the following tables (Tables 10 and 11).

In addition, the $^1$H-NMR data (no symbol: 400 MHz NMR, symbol "*": 300 MHz NMR) and the LC-Mass data of the intermediate compounds synthesized in each step of Example 1 are shown in the following Tables 12 and 13.

Example 1-1

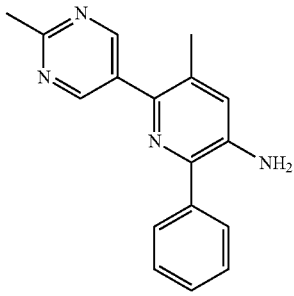

Example 1-2

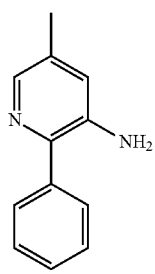

Example 1-3

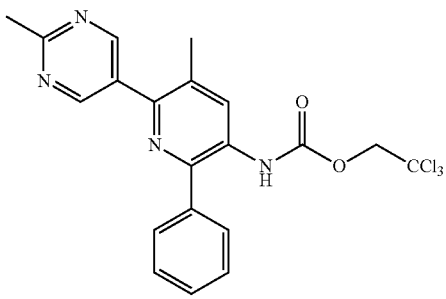

Example 1-4

Example 1-5

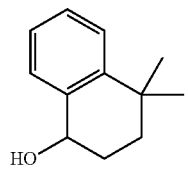

Example 1-6

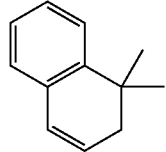

Example 1-7

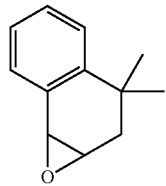

Example 1-8

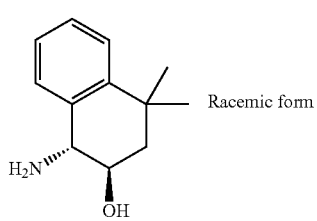

Racemic form

Example 1-9

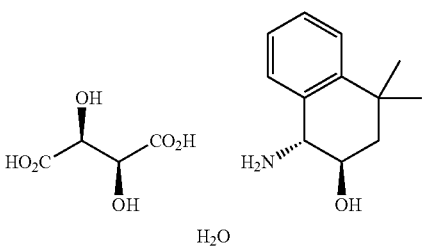

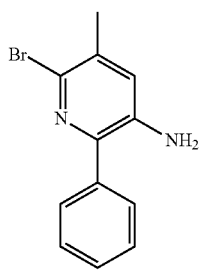

H$_2$O

Example 1

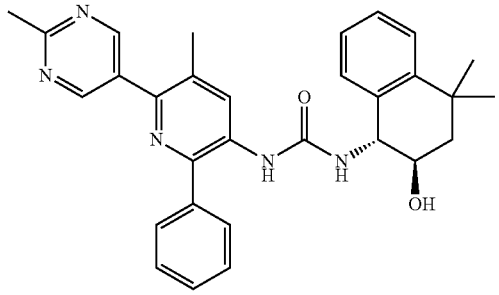

(Example 2) Type I Crystal of 1-((1R,2R)-2-hydroxy-4,4-dimethyl-1,2,3,4-tetrahydronaphthalen-1-yl)-3-(5-methyl-6-(2-methylpyrimidin-5-yl)-2-phenylpyridin-3-yl)urea The compound (1) (15.0 g) obtained according to the method of (Example 1) was suspended in a mixture solution of ethanol (105 mL) and water (45 mL), and the mixture was stirred at 72° C. for 30 minutes. Ethanol (28 mL) and water (12 mL) were further added, and the mixture was stirred at the same temperature for 40 minutes to be dissolved completely. After stirring at the same temperature for an additional 30 minutes, it was allowed to cool to room temperature, and then stirred at the same temperature for 15 hours. The precipitated crystal was collected, washed with a mixture of ethanol-water (1:4) and water, and then dried under reduced pressure to obtain the product (12.7 g). A mixture solvent of ethanol-water (1:9) (127 mL) was added to this product, and the mixture was stirred at 74° C. for 40 minutes, and allowed to cool to room temperature. The precipitated crystal was collected to obtain the title compound (11.9 g) as a white solid (Type I crystal of compound (1)).

Figure 9:
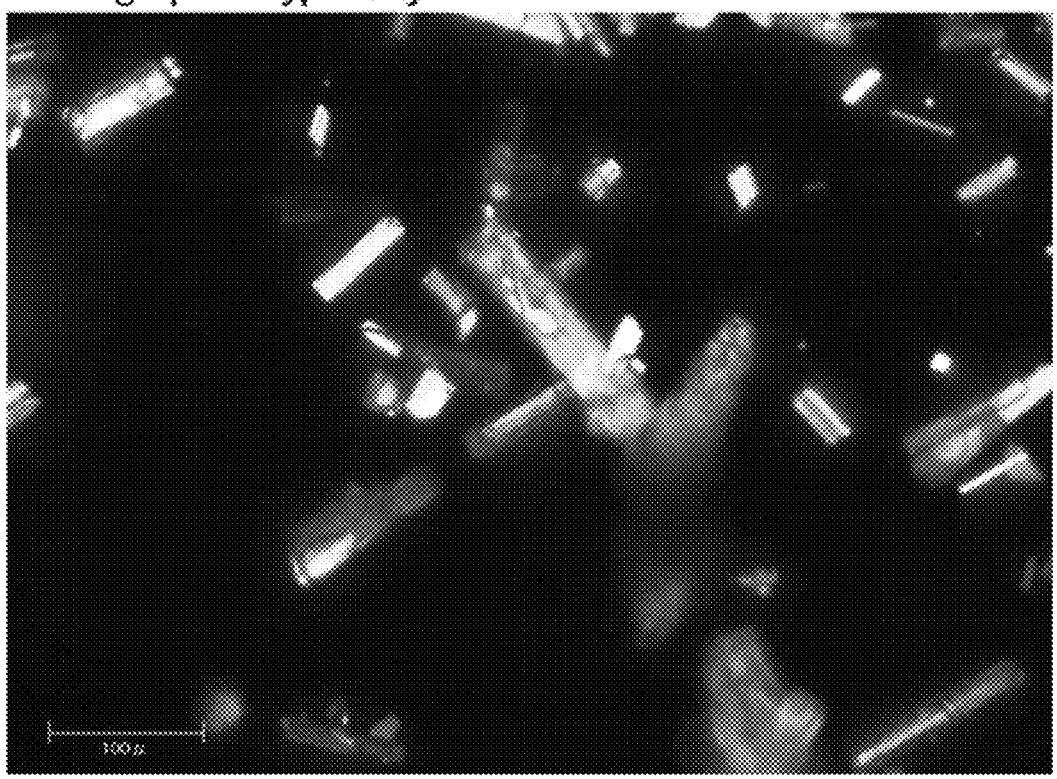
FIG. 9 is a micrograph of the type I crystal of the compound (1) in Example 2.

The result of the measurement of powder X-ray diffraction of the obtained type I crystal of the compound (1) are shown in FIG. 1, and the characteristic peaks of the type I crystal, are shown in Table 2. The FT-IR spectral data of the type I crystal is shown in FIG. 2. The spectral data of differential scanning calorimetry (DSC) and thermogravimetric analysis (TGA) of the type I crystal are shown in FIG. 8, and a micrograph of the type I crystal is shown in FIG. 9.

TABLE 2

Powder X-ray diffraction data of type I crystal (characteristic peaks)

| 2 Θ (°) | Relative Intensity (%) |
|---|---|
| 9.2 | 72.5 |
| 11.2 | 100 |
| 12.9 | 58.1 |
| 18.0 | 54.6 |
| 18.4 | 51.7 |
| 21.3 | 53.4 |
| 23.5 | 88.5 |
| 24.0 | 56.2 |
| 24.6 | 68.9 |
| 25.7 | 63.1 |
| — | — |

(Example 3) Type III Crystal of 1-((1R,2R)-2-hydroxy-4,4-dimethyl-1,2,3,4-tetrahydronaphthalen-1-yl)-3-(5-methyl-6-(2-methylpyrimidin-5-yl)-2-phenylpyridin-3-yl)urea The compound (1) (0.76 g) obtained according to (Example 1) was suspended in methyl tert-butyl ether (MTBE) (11.5 mL), and the mixture was stirred at room temperature for 29 hours. The precipitated crystal was collected, washed with MTBE, and dried under reduced pressure to obtain the product (0.66 g). The product was suspended in MTBE (9.5 mL), and the mixture was stirred at room temperature for 98 hours. The precipitated crystal was collected to obtain the title compound (0.57 g) as a white solid (type III crystals of compound (1)).

The result of powder X-ray diffraction of the obtained type III crystal of the compound (1) are shown in FIG. 3, and the characteristic peaks of type III crystal are shown in Table 3. The FT-IR spectral data of the type III crystal is shown in FIG. 4. The spectral data of the DSC and TGA of the type III crystal are shown in FIG. 10.

TABLE 3

Powder X-ray diffraction data of type III crystal (characteristic peaks)

| 2 Θ (°) | Relative Intensity (%) |
|---|---|
| 6.8 | 53.4 |
| 10.3 | 100 |
| 14.3 | 36.7 |
| 15.3 | 39.8 |
| 17.6 | 39.7 |
| 19.7 | 52.4 |
| 20.9 | 40.5 |
| 21.6 | 35.8 |
| 22.3 | 33.3 |
| 22.6 | 39.0 |
| — | — |

(Example 4) Type V Crystal of 1-((1R,2R)-2-hydroxy-4,4-dimethyl-1,2,3,4-tetrahydronaphthalen-1-yl)-3-(5-methyl-6-(2-methylpyrimidin-5-yl)-2-phenylpyridin-3-yl)urea The type I crystal (2.12 g) of the compound (1) obtained in (Example 2) was suspended in a mixture solution of acetone (11 mL) and n-heptane (11 mL), and the mixture was stirred at room temperature for 1 hour. n-Heptane (22 mL) was added to this suspension, and the precipitate was collected to obtain the title compound (1.90 g) as a white solid (type V crystals of compound (1)).

Figure 12:
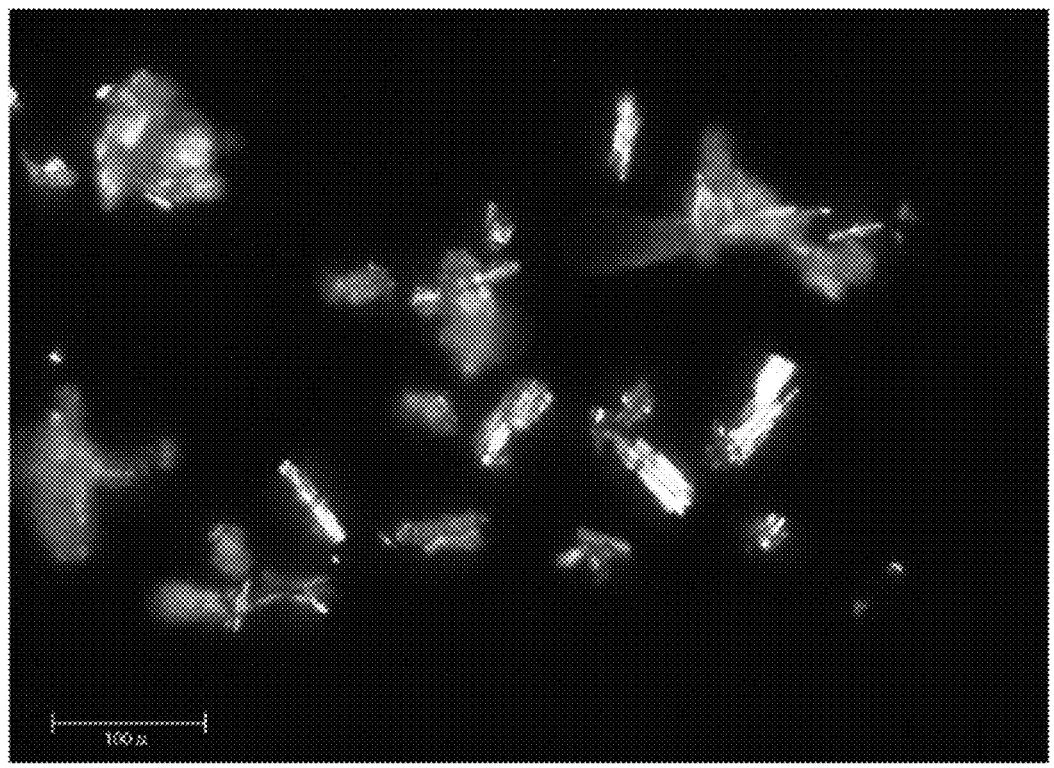
FIG. 12 is a micrograph of the type V crystal of the compound (1) in Example 4.

The result of powder X-ray diffraction of the obtained type V crystal of the compound (1) are shown in FIG. 5, and the characteristic peaks of the type V crystal are shown in Table 4. The FT-IR spectral data of the type V crystal is shown in FIG. 6. The spectral data of DSC and TGA of the type V crystal is shown in FIG. 11, and a micrograph of the type V crystal is shown in FIG. 12.

TABLE 4

Powder X-ray diffraction data of type V crystal (characteristic peaks)

| 2 Θ (°) | Relative Intensity (%) |
|---|---|
| 7.2 | 100 |
| 10.8 | 83.1 |

TABLE 4-continued

Powder X-ray diffraction data of type V crystal (characteristic peaks)

| 2 Θ (°) | Relative Intensity (%) |
|---|---|
| 11.9 | 41.3 |
| 14.5 | 40.2 |
| 18.8 | 77.5 |
| 22.3 | 29.0 |
| 23.9 | 47.8 |
| 24.2 | 27.0 |
| 26.0 | 28.3 |
| 27.9 | 39.4 |
| — | — |
| — | — |

(Example 5) Type VI Crystal of 1-((1R,2R)-2-hydroxy-4,4-dimethyl-1,2,3,4-tetrahydronaphthalen-1-yl)-3-(5-methyl-6-(2-methylpyrimidin-5-yl)-2-phenylpyridin-3-yl)urea The compound (1) (3.94 g) obtained according to (Example 1) was suspended in a mixture solution of ethanol (28 mL) and water (12 mL), and the mixture was stirred at 80° C. for 20 minutes to be dissolved completely. After allowing to cool to room temperature, the mixture was stirred at the same temperature for 17 hours. The precipitated crystal was collected, washed with a mixture of ethanol-water (7:3), and then dried under reduced pressure to obtain the title compound (3.29 g) as a white solid (type VI crystal of the compound (1)).

The result of powder X-ray diffraction of the obtained type VI crystal of the compound (1) are shown in FIG. 7, and the characteristic peaks of the type VI crystal are shown in Table 5.

TABLE 5

Powder X-ray diffraction data of type VI crystal (characteristic peaks)

| 2 Θ (°) | Relative Intensity (%) |
|---|---|
| 6.9 | 30.3 |
| 9.2 | 29.9 |
| 11.1 | 100 |
| 13.3 | 35.5 |
| 18.5 | 33.5 |
| 19.0 | 35.4 |
| 22.3 | 38.0 |
| 22.8 | 29.8 |
| 23.4 | 54.9 |
| 24.2 | 40.5 |
| — | — |
| — | — |

(Test Example 1) Determination of Equilibrium Solubility (Determination of Solubility in Phosphate Buffer Solution with PH 6.8)

Each of the equilibrium solubilities (solubility in phosphate buffer solution with pH 6.8) of Type I (Example 2), III (Example 3), V (Example 4) and VI crystals (Example 5) of 1-((1R,2R)-2-hydroxy-4,4-dimethyl-1,2,3,4-tetrahydronaphthalen-1-yl)-3-(5-methyl-6-(2-methylpyrimidin-5-yl)-2-phenylpyridin-3-yl)urea obtained in the above (Example 2) to (Example 5) was determined as follows:

<Determination Method>
(1) Preparation of Phosphate Buffer Solution (pH 6.8):

Water was added a weighed potassium dihydrogen phosphate of 2.7g to make 100 mL volume to prepare 0.2 mol/L potassium dihydrogen phosphate solution. Water was added a weighed disodium hydrogen phosphate decahydrate of 7.2 g to make 100 mL volume to prepare 0.2 mol/L disodium hydrogen phosphate solution. A pH 6.8 phosphate buffer solution was prepared by diluting a mixture of 0.2 mol/L potassium dihydrogen phosphate solution (14.8 mL) and 0.2 mol/L disodium hydrogen phosphate solution (10.0 mL) with water (173.6 mL).
(2) Measurement Method Approximately 1 mg of the each crystal from (Example 2) to (Example 5) was weighed into a screw tube, and a pH 6.8 phosphate buffer solution (1 mL) was added. An isothermal shaker (M-BR-022UP) was used to incubate the sample at 37° C. and 1000 rpm for 24 hours. 100 µL solution were sampled at 1, 2, 6, and 24 hours after the start of incubation, and were filtered using a centrifuge (HITACHI, Himac cF 9RX, at 25° C., at 1500 rpm, for 30 seconds) with a filter (Millipore: Multiscreen, MSSLBPC10) so as to remove insoluble materials. A 20 µL of the filtrate was quantified, and diluted with a solution (180 µL, pH 9.0) of 20 vol % tetrahydrofuran and 80 vol % ammonium bicarbonate aqueous solution (10 mM). A 10 µL of the prepared solution was quantified, and diluted with a solution (190 µL, pH 9.0) of 20 vol % tetrahydrofuran and 80 vol % ammonium bicarbonate aqueous solution (10 mM). The prepared solution was analyzed by ultra performance liquid chromatography (UPLC) under the following measurement conditions, and the concentration of the compound in the solution was calculated based on a previously prepared calibration curve. Three times of measurements were made for each example compound, and the mean values and standard deviations of the three measurements are shown as a result in Table 6.

TABLE 6

| Test compound | | Solubility (µg/ml) |
|---|---|---|
| Compound of Example 2 | Mean value | 33.2 |
| (Type I crystal) | Standard deviation | 3.0 |
| Compound of Example 3 | Mean value | 66.0 |
| (Type III crystal) | Standard deviation | 2.2 |
| Compound of Example 4 | Mean value | 60.1 |
| (Type V crystal) | Standard deviation | 6.2 |
| Compound of Example 5 | Mean value | 41.1 |
| (Type VI crystal) | Standard deviation | 2.0 |

<UPLC Measurement Conditions>
  Equipment: ACQUITY UPLC H-Class (Waters)
  Detector: PDA (200-500 nm)
  Column: BEH C18 2.1×50 mm
  Measurement wavelength: 270 nm
  Column temperature: 40° C.
  Injection amount: 10 µL
  Mobile phase:
  Solvent A, acetonitrile;
  Solvent B, 10 mM ammonium bicarbonate aqueous solution (pH 9.0)
  Gradient conditions:

| 0 min | A5%, B95% |
|---|---|
| 0.5 min | A5%, B95% |
| 2.5 min | A90%, B10% |
| 3.5 min | A90%, B10% |
| 3.7 min | A5%, B95% |
| 5 min | A5%, B95% |

Flow rate: 0.7 mL per minute (Test Example 2) Storage Stability Test

The type I (Example 2), III (Example 3), V (Example 4) and VI (Example 5) crystals (each about 20 mg) of 1-((1R, 2R)-2-hydroxy-4,4-dimethyl-1,2,3,4-tetrahydronaphthalen-1-yl)-3-(5-methyl-6-(2-methylpyrimidin-5-yl)-2-phenylpyridin-3-yl)urea obtained in the above Examples 2 to 5 were stored in glass bottles under the respective conditions described in Table 7. After completion of the storage period, the retrieved sample was confirmed on the purity by high performance liquid chromatography and on the crystal form by powder X-ray diffraction analysis as in the Examples. The results are shown in Table 7.

TABLE 7

Storage Stability

| Test compound | Storage conditions | Chemical purity (%) | Crystalline form after completion of storage period |
|---|---|---|---|
| Compound of Example 2 (Type I crystal) | Before the test | 99.8 | Type I crystal |
| | 25° C./60% RH, open for 1 month | 99.8 | Type I crystal |
| | 25° C./60% RH, closed for 1 month | 99.8 | Type I crystal |
| | 40° C./75% RH, open for 1 month | 99.8 | Type I crystal |
| | 40° C./75% RH, closed for 1 month | 99.8 | Type I crystal |
| Compound of Example 3 (Type III crystal) | Before the test | 100.0 | Type III crystal |
| | 25° C./60% RH, open for 1 month | 100.0 | Type III crystal |
| | 25° C./60% RH, closed for 1 month | 100.0 | Type III crystal |
| | 40° C./75% RH, open for 1 month | 100.0 | Type III crystal |
| | 40° C./75% RH, closed for 1 month | 100.0 | Type III crystal |
| Compound of Example 4 (Type V crystal) | Before the test | 99.8 | Type V crystal |
| | 25° C./60% RH, open tor 1 month | 99.8 | Type V crystal |
| | 25° C./60% RH, closed for 1 month | 99.8 | Type V crystal |
| | 40° C./75% RH, open for 1 month | 99.8 | Type V crystal |
| | 40° C./75% RH, closed for 1 month | 99.8 | Type V crystal |
| Compound of Example 5 (Type VI crystal) | Before the test | 99.8 | Type VI crystal |
| | 25° C./60% RH, open for 1 month | 99.9 | Type I crystal |
| | 25° C./60% RH, closed for 1 month | 99.9 | Type VI crystal |
| | 40° C./75% RH, open for 1 month | 99.9 | Type I crystal |
| | 40° C./75% RH, closed for 1 month | 99.9 | Mixture of Type VI crystal with Type I crystal |

The results of (Test Example 2) showed that the type I and V crystals of the present invention were chemically and physically stable over the test period. And also, during this period, no moisture absorption was observed in the type I and V crystals.

Therefore, the qualities of these crystals as the drug substance are maintained within the specifications for a long period of time, and these crystal can be easily processed into a drug product and can be used in drug products.

In addition, it was confirmed that the type VI crystal were transferred to the type I crystal during storage (open system) as described above (see, Test Example 2).

(Test Example 3) Photostability Test

The type I (Example 2), III (Example 3), V (Example 4), and VI (Example 5) crystals (each about 20 mg) of 1-((1R, 2R)-2-hydroxy-4,4-dimethyl-1,2,3,4-tetrahydronaphthalen-1-yl)-3-(5-methyl-6-(2-methylpyrimidin-5-yl)-2-phenylpyridin-3-yl)urea obtained in the above Examples 2 to 5 were placed in a transparent plastic container and covered, and were subjected to photostability test according to the ICH Q1B (Guidelines on Photostability Testing of New Active Substances and Medicinal Products) described in Table 8 (Here, the photostability test samples were stored at about 25° C. under separate lamps which respectively emits visible light and UV-A light so that the total light exposure should be 1.2 million lux hours and 200 W hours/m$^2$ or more, respectively. A 5-day study should be designated as "0.5 ICH" and a 10-day study as "1 ICH"). Table 9 shows the results of a similar tests in which plastic container containing the test compound was shielded from light by aluminum foil. After completion of the test, the retrieved sample was confirmed on the purity by high performance liquid chromatography and on the crystal form by powder X-ray diffraction analysis as in the Examples. The results are shown in Tables 8 and 9.

TABLE 8

Photostability (Exposure)

| Test compound | Test conditions | Chemical purity (%) | Crystalline form after completion of test |
|---|---|---|---|
| Compound of Example 2 (Type I crystal) | Before the test | 99.8 | Type I crystal |
| | 0.5 ICH | 99.2 | Type I crystal |
| | 1 ICH | 98.9 | Type I crystal |
| Compound of Example 3 (Type III crystal) | Before the test | 100.0 | Type III crystal |
| | 0.5 ICH | 100.0 | Type III crystal |
| | 1 ICH | 100.0 | Type III crystal |
| Compound of Example 4 (Type V crystal) | Before the test | 99.9 | Type V crystal |
| | 0.5 ICH | 99.8 | Type V crystal |
| | 1 ICH | 99.8 | Type V crystal |
| Compound of example 5 (Type VI crystal) | Before the test | 99.8 | Type VI crystal |
| | 0.5 ICH | 99.7 | Type I crystal |
| | 1 ICH | 99.5 | Type I crystal |

TABLE 9

Photostability (Shielded/Under Light Shielding)

| Test compound | Test conditions | Chemical purity (%) | Crystalline form after completion of test |
|---|---|---|---|
| Compound of Example 2 (Type I crystal) | Before the test | 99.8 | Type I crystal |
| | 0.5 ICH | 99.8 | Type I crystal |
| | 1 ICH | 99.8 | Type I crystal |
| Compound of Example 3 (Type III crystal) | Before the test | 100.0 | Type III crystal |
| | 0.5 ICH | 100.0 | Type III crystal |
| | 1 ICH | 100.0 | Type III crystal |
| Compound or Example 4 (Type V crystal) | Before the test | 99.9 | Type V crystal |
| | 0.5 ICH | 99.9 | Type V crystal |
| | 1 ICH | 99.9 | Type V crystal |
| Compound or Example 5 (Type VI crystal) | Before the test | 99.8 | Type VI crystal |
| | 0.5 ICH | 99.9 | Type I crystal |
| | 1 ICH | 99.9 | Type I crystal |

From the above results, it has been found that the type I, III and V crystals of the present invention are stable against light. However, it was confirmed that the type VI crystal is unstable against light and transferred to the type I crystal during the above tests.

From the above results, the crystals of the present invention have high crystallinity as shown in Examples 2 to 5, high solubility as shown in Test Example 1, high storage stability as shown in Test Example 2, and high photostability as shown in Test Example 3. Thus, these crystals are easily handled during drug product manufacture as drug substances, and are suitable for drug substances and drug formulations.

TABLE 10

| Example | NMR data (δ: ppm) <*300 MHz> |
|---|---|
| 1 | (CDCl3) δ: 8.88 (2 H, s), 8.46 (1 H, s), 7.66-7.62 (2 H, m), 7.55-7.42 (3 H, m), 7.35-7.17 (4 H, m), 6.89 (1 H, br s), 4.93 (1 H, d, J = 8 Hz), 4.88-4.78 (1 H, m), 3.96-3.86 (1 H, m), 3.10 (1 H, br s), 2.80 (3 H, s), 2.48 (3 H, s), 1.96 (1 H, dd, J = 13, 4 Hz), 1.80 (1 H, dd, J = 13, 13 Hz), 1.38 (3 H, s), 1.29 (3 H, s) |

TABLE 11

| Example | MS-ESI (m/z) [M + H]+ | Retention time (min) | Method |
|---|---|---|---|
| 1 | 494 | 1.09 | A |

*:[M+Na]+

TABLE 12

| Example | NMR data (δ: ppm) <*300 MHz> |
|---|---|
| 1-1 | (CDCl3) δ: 7.97 (1H, s), 7 69-7.63 (2H, m), 7.50-7.43 (2H, m), 7.42-7.33 (1H, m), 6.87 (1H, s), 3.79 (2H, br s), 2.29 (3 H, s) |
| 1-2 | *(CDCl3) δ: 7.67-7.61 (2H, m), 7.50-7.42 (2H, m), 7.41-7.34 (1H, m), 6.93 (1H, d, J = 1 Hz), 3.81 (2H, br s), 2.34 (3H, s) |
| 1-3 | *(CDCl3) δ: 8.96 (2H, s), 7.74-7.69 (2H, m), 7.53-7.46 (2H, m), 7.44-7.38 (1H, m), 7.02 (1H, s), 3.99 (2H, br s), 2.41 (3H, s), 1.64 (3H, s) |
| 1-4 | *(CDCl3) δ: 8.89 (2H, s), 8. 41 (1H, br s), 7.67-7.61 (2H, m), 7.60-7.47 (3H, m), 7.06 (1H, br s), 4.86 (2H, s), 2.81 (3H, s), 2.50 (3H, s) |
| 1-5 | *(CDCl3) δ: 7.43 (1H, dd, J = 8.2 Hz), 7.35 (1H, dd, J = 8, 2 Hz), 7.30-7.17 (2H, m), 4.82-4.69 (1H, m), 2.16-2.04 (1H, m), 1.97-1.83 (2H, m), 1.74-1.54 (1H, m), 1.35 (3H, s), 1.26 (3H, s) |
| 1-6 | (CDCl3) δ: 7.30 (1H, d, J = 7 Hz), 7.22-7.12 (2H, m), 7.04 (1H, dd, J = 7, 2 Hz), 6.48-6.43 (1H, m), 5.97-5.91 (1H, m), 2.26 (2H, dd, J = 4, 2 Hz), 1.28 (6H, s) |
| 1-7 | *(CDCl3) δ: 7.45 (1H, dd, J = 7, 1 Hz), 7.40-7.31 (2H, m), 7.25-7.18 (1H, m), 3.88 (1H, d, J = 4 Hz), 3.77-3.73 (1H, m), 2.24 (1H, dd, J = 15, 3 Hz), 1.86 (1H, dd, J = 15, 1 Hz), 1.37 (3H, s), 1.33 (3H, s) |
| 1-8 | (DMSO-D6) δ: 7.60 (1H, dd, J = 6, 3 Hz), 7.29-7.25 (1H, m), 7.17-7.09 (2H, m), 4.84 (1H, d, J = 4 Hz), 3.49-3.28 (1H, m), 1.88 (2H, br s), 1.77 (1H, dd, J = 13, 3 Hz), 1.62-1.54 (1H, m), 1.27 (3H, s), 1.22 (3H, s) |
| 1-9 | *(CD3OD) δ: 7.50-7.26 (4H , m), 4.40 (2H, s), 4.19 (1H, d, J = 9 Hz), 4.04-3.93 (1H, m), 2.01 (1H, dd, J = 13, 3 Hz), 1.82 (1H, dd, J = 13, 13 Hz), 1.39 (3H, s), 1.37 (3H, s) |

TABLE 13

| Example | MS-ESI (m/z) [M + H]+ | Retention time (min) | Method |
|---|---|---|---|
| 1-1 | 185 | 0.58 | A |
| 1-2 | 263, 265 | 1.02 | A |
| 1-3 | 277 | 0.66 | A |
| 1-4 | 451, 453, 455 | 1.12 | A |
| 1-5 | 159 (—OH) | 1.04 | A |
| 1-6 | 159 | 1.25 | A |
| 1-8 | 214* | 0.70 | A |

*:[M+Na]+

INDUSTRIAL APPLICABILITY

Since the crystals of the present invention can be understood to exhibit excellent TrkA inhibitory effect, it is possible to provide clinically useful prevention and/or therapeutic agents for diseases such as pain.

The crystals of the present invention are also useful as crystals of the drug substance. Providing crystals of compound (1) as described above makes it possible to provide superior pharmaceutical compositions, and is useful.

Although some of the specific embodiments of the present invention have been described in detail above, various modifications and variations can be made to the specific embodiments by those skilled in the art without substantially departing from the teachings and advantages of the present invention. Accordingly, all such modifications and variations are within the spirit and scope of the invention as claimed in the claims.

What is claimed is:

1. A type I crystal of 1-((1R,2R)-2-hydroxy-4,4-dimethyl-1,2,3,4-tetrahydronaphthalen-1-yl)-3-(5-methyl-6-(2-methylpyrimidin-5-yl)-2-phenylpyridin-3-yl)urea having characteristic peaks at least at diffraction angles (2θ) of 9.2±0.2, 11.2±0.2, 12.9±0.2, 18.0±0.2, 18.4±0.2, 21.3±0.2, 23.5±0.2, 24.0±0.2, 24.6±0.2, and 25.7±0.2 (°) in x-ray powder diffraction.

2. A type I crystal of 1-((1R,2R)-2-hydroxy-4,4-dimethyl-1,2,3,4-tetrahydronaphthalen-1-yl)-3-(5-methyl-6-(2-methylpyrimidin-5-yl)-2-phenylpyridin-3-yl) urea, characterized by an x-ray powder diffraction pattern shown in FIG. 1., wherein an error of ±0.2 (°) in diffraction angle (2θ) is allowed for each characteristic peaks of the x-ray powder diffraction pattern.

3. The type I crystal according to claim 1, having an extrapolated melting point onset temperature of 131° C. in differential scanning calorimetry measurement (DSC measurement).

4. The type I crystal according to claim 1, having a columnar crystal form.

5. A method for producing the type I crystal according to claim 1, the method comprising a step of suspending 1-((1R,2R)-2-hydroxy-4,4-dimethyl-1,2,3,4-tetrahydronaphthalen-1-yl)-3-(5-methyl-6-(2-methylpyrimidin-5-yl)-2-phenylpyridin-3-yl) urea with a mixed solvents of alcohol solvents and water;

a step of dissolving the resulting mixed solution under heating and stirring;

a step of stirring the dissolved mixed solution at the heating temperature; and a step of cooling the mixed solution with stirring to room temperature to obtain the crystal.

6. A pharmaceutical composition comprising the crystal according to claim 1, as an active ingredient.

7. The type I crystal according to claim 2, having an extrapolated melting point onset temperature of 131° C. in differential scanning calorimetry measurement (DSC measurement).

8. The type I crystal according to claim 2, having a columnar crystal form.

9. A method for producing the type I crystal according to claim 2, the method comprising a step of suspending 1-((1R,2R)-2-hydroxy-4,4-dimethyl-1,2,3,4-tetrahydronaphthalen-1-yl)-3-(5-methyl-6-(2-methylpyrimidin-5-yl)-2-phenylpyridin-3-yl) urea with a mixed solvents of alcohol solvents and water;

a step of dissolving the resulting mixed solution under heating and stirring;

a step of stirring the dissolved mixed solution at the heating temperature;

and a step of cooling the mixed solution with stirring to room temperature to obtain the crystal.

10. A pharmaceutical composition comprising the crystal according to claim 2, as an active ingredient.

* * * * *